US011723828B2

(12) United States Patent
Cohen et al.

(10) Patent No.: US 11,723,828 B2
(45) Date of Patent: Aug. 15, 2023

(54) CONTROLLED STIMULATION DEVICE

(71) Applicant: Lutronic Aesthetics, Inc., Billerica, MA (US)

(72) Inventors: Richard H. Cohen, San Rafael, CA (US); David W. Sanso, Morrison, CO (US); Jamie R. Korte, Golden, CO (US)

(73) Assignee: Lutronic Aesthetics, Inc., Billerica, MA (US)

( * ) Notice: Subject to any disclaimer, the term of this patent is extended or adjusted under 35 U.S.C. 154(b) by 1032 days.

(21) Appl. No.: 16/514,476

(22) Filed: Jul. 17, 2019

(65) Prior Publication Data

US 2020/0022866 A1    Jan. 23, 2020

Related U.S. Application Data

(60) Provisional application No. 62/699,450, filed on Jul. 17, 2018.

(51) Int. Cl.
*A61H 7/00* (2006.01)
*A61N 1/40* (2006.01)
*A61N 5/06* (2006.01)

(52) U.S. Cl.
CPC ............ *A61H 7/005* (2013.01); *A61N 1/40* (2013.01); *A61N 5/0616* (2013.01); *A61H 2201/10* (2013.01); *A61H 2201/5043* (2013.01); *A61N 2005/0644* (2013.01)

(58) Field of Classification Search
CPC .......... A61H 7/005; A61H 2201/10; A61H 2201/5043; A61H 7/001; A61H 2039/005; A61H 39/04; A61H 39/08; A61H 23/02; A61N 1/40; A61N 5/0616; A61N 2005/0644; A61N 1/328; A63F 2007/0094; A63F 2009/345; A63B 21/005; A63B 21/0052; A63B 21/0056; A63B 21/0057; A63B 21/012; A61B 2018/00452; A61B 18/203; A61B 2018/2253; A61M 5/422
See application file for complete search history.

(56) References Cited

U.S. PATENT DOCUMENTS

| | | | |
|---|---|---|---|
| 5,879,337 | A | 3/1999 | Kuracina et al. |
| 6,001,080 | A | 12/1999 | Kuracina et al. |
| 6,083,233 | A | 7/2000 | Kreutz et al. |
| 6,293,953 | B1 | 9/2001 | Kreutz et al. |
| 6,415,800 | B2 | 7/2002 | Poisson et al. |

(Continued)

FOREIGN PATENT DOCUMENTS

| | | |
|---|---|---|
| WO | 2008002515 A2 | 1/2008 |
| WO | 2009117437 A1 | 9/2009 |
| WO | 2017164430 A1 | 9/2017 |

OTHER PUBLICATIONS

International Search Report and Written Opinion, PCT/US2019/042278, dated Nov. 6, 2019, 15 pages.

(Continued)

*Primary Examiner* — Ahmed M Farah
*Assistant Examiner* — Sebastian X Lukjan
(74) *Attorney, Agent, or Firm* — Nelson Mullins Riley & Scarborough LLP; Anthony A. Laurentano

(57) ABSTRACT

A controlled stimulation device used either alone or in conjunction with a treatment device to reduce amount of pain a patient may experience during a treatment with the treatment device.

87 Claims, 18 Drawing Sheets

(56) References Cited

U.S. PATENT DOCUMENTS

| | | |
|---|---|---|
| 6,443,929 B1 | 9/2002 | Kuracina et al. |
| 6,622,943 B2 | 9/2003 | Poisson et al. |
| 6,629,959 B2 | 10/2003 | Kuracina et al. |
| 6,730,099 B1 | 5/2004 | Kreutz et al. |
| 6,860,871 B2 | 3/2005 | Kuracina et al. |
| 7,066,908 B2 | 6/2006 | Kuracina et al. |
| 7,147,645 B2 | 12/2006 | Sanchez-Martinez et al. |
| 7,195,635 B2 | 3/2007 | Kreutz et al. |
| 7,211,090 B2 | 5/2007 | Kreutz et al. |
| 7,534,231 B2 | 5/2009 | Kuracina et al. |
| 7,927,314 B2 | 4/2011 | Kuracina et al. |
| 8,100,857 B2 | 1/2012 | Kuracina et al. |
| 8,332,982 B2 | 12/2012 | Braun et al. |
| 8,414,539 B1 | 4/2013 | Kuracina et al. |
| 8,444,605 B2 | 5/2013 | Kuracina et al. |
| 8,545,454 B2 | 10/2013 | Kuracina et al. |
| 9,919,168 B2 | 3/2018 | Altshuler et al. |
| 2002/0128665 A1 | 9/2002 | Kreutz et al. |
| 2005/0177071 A1 | 8/2005 | Nakayama et al. |
| 2005/0235439 A1 | 10/2005 | Braun et al. |
| 2006/0078844 A1 | 4/2006 | Goldman et al. |
| 2008/0132886 A1 | 6/2008 | Cohen et al. |
| 2009/0105696 A1 | 4/2009 | Lee et al. |
| 2009/0172900 A1 | 7/2009 | Brown, Jr. et al. |
| 2012/0116271 A1 | 5/2012 | Caruso et al. |
| 2012/0245497 A1* | 9/2012 | Nicholls ............... A61H 7/005 601/136 |
| 2013/0066237 A1 | 3/2013 | Smotrich et al. |
| 2014/0194789 A1 | 7/2014 | Ko |
| 2014/0358200 A1 | 12/2014 | Ko |
| 2016/0067424 A1 | 3/2016 | Sealfon et al. |
| 2017/0112574 A1 | 4/2017 | Cohen et al. |

OTHER PUBLICATIONS

International Preliminary Report on Patentability, PCT/US2019/042278, dated Jan. 28, 2021, 9 Pages.

* cited by examiner

CONTROLLED STIMULATION DEVICE

CROSS-REFERENCE TO RELATED APPLICATION

The present application claims the benefit and priority of, under 35 U.S.C. § 119(e), U.S. Provisional Patent Application No. 62/699,450, filed on Jul. 17, 2018, entitled COUNTER-STIMULATION DEVICE, which is hereby incorporated herein by reference in its entirety for all that it teaches and for all purposes.

FIELD OF THE DISCLOSURE

The present disclosure relates generally to devices, methods and systems associated with a controlled stimulation device that can be used either alone or in conjunction with a treatment device.

BACKGROUND

Certain types of medical, surgical, aesthetic or other treatment devices potentially cause discomfort or pain. Such treatment devices include, for example, electromagnetic energy emitting devices (e.g., light-emitting devices, lasers, radio-frequency energy emitting devices, etc.) or injection/insertion devices (e.g., needles, which penetrate a patient's epithelium, other skin layers, or other tissues during treatment).

Nociception is the sensory nervous system's response to certain harmful or potentially harmful stimuli. Upon stimulation of the sensory nerve cells, which are referred to as nociceptors, a signal is produced that travels along a chain of nerve fibers via the spinal cord to the brain where it can trigger a variety of physiological and behavioral responses and usually results in the patient's experience of cognitive and emotional pain.

SUMMARY

Controlled stimulation devices, methods and systems are disclosed that can repeatedly engage and disengage a patient's skin, e.g., the epidermis and/or underlying tissue, in order to activate the patient's nociceptors during a treatment session reducing the discomfort and pain that might otherwise be triggered by a treatment device.

In one aspect, a controlled stimulation device for use during a treatment procedure, e.g., a dermatological treatment procedure, is disclosed, which comprises at least one skin reference element having a distal end that defines a skin surface plane when placed in contact with a region of skin to be treated, a base element movable relative to the skin reference element and one or more elongated members coupled to the base element, such that distal ends of elongated members can move between at least two positions, one position being a stowed position at or behind the distal end of the skin reference member and the other position being a deployed position in which the distal end(s) of the elongated member(s) protrude to contact or penetrate the skin region. In some embodiments, the elongated member(s) protrude distally beyond the distal end of the skin reference element to contact or penetrate the skin region. In certain preferred embodiments, a plurality of flexible elongated members are deployed to penetrate the patient's skin to stimulate the patient's nociceptors to reduce the discomfort and pain that would be otherwise triggered by the treatment procedure.

In some embodiments, the device includes a chassis to which the at least one skin reference element can be coupled. The chassis can also include a mount that is coupled to the base element such that the distal ends of elongated flexible members can move between the stowed position and the deployed position. In some embodiments, the stowed and the deployed positions are separated by a distance in a range of about 0.1 mm to about 15 mm, e.g., in a range of about 0.25 mm to about 0.75 mm.

The chassis can be further adapted to couple with a skin treatment handpiece. The skin treatment handpiece can include an energy source for generating energy for skin treatment. By way of example, such an energy source can be a light energy source or a radio frequency energy source. In other embodiments, the handpiece can be a mechanical treatment device. For example, in some embodiments, the treatment device can apply a treatment to the patient's skin via needle insertion or scalpel cut, or other mechanical treatment modalities.

In some embodiments, the skin surface element is disposed distally relative to the base element. Each of the base element and the skin surface element can include an aperture though which treatment energy can be applied to the skin. In some embodiments, the elongated flexible members are arranged so as to at least partially surround the aperture.

The device can include a motor that is coupled to the base element via a linkage for inducing movement of the base element. In some embodiments, the linkage can impart an axial motion to the base element. In some embodiments, the linkage can include a cam, .e.g, an axial (cylindrical) or tangent cam. In some embodiments, the linkage can include an eccentric shaft that is coupled to the base element. In some embodiments, the linkage can include a cylindrical cam that is coupled to a drive shaft, where the drive shaft is coupled to the base element.

The distal ends of the elongated members can have a variety of different shapes. In many embodiments, any shape that allows facile penetration of the distal ends of the elongated members into the skin can be employed. For example, the shape of the distal ends can be at least one of a round point, a star point, a cross point, a tapered face, a beveled face (e.g., beveled at an angle between 30 and 60 degrees, preferably about 45 degrees), a multi-facet face, and/or a conical, spherical, elliptical, or hyper-elliptical shape, without or without grooves, e.g., micro-ridges or micro-lines. In some embodiments, the distal ends of the elongated flexible members can have a stop, e.g., in form of a collar, that limits the penetration depth of the distal ends into the patient's skin. Further, in some embodiments, Further, in some embodiments, the distal ends can have a shape that can facilitate causing depression into the skin upon contact without penetrating the skin. For example, in some such embodiments, the distal ends can have a substantially flat end.

In some embodiments, the plurality of flexible elongated members have a length in a range of about 0.05 mm to about 150 mm. In some embodiments, the plurality of elongated flexible members have a cross-sectional area in a range of about 0.02 $mm^2$ to about 20 $mm^2$. In some embodiments, the plurality of elongated flexible members are substantially cylindrical. In some such embodiments, the elongated flexible members can have a diameter in a range of about 25 microns to about 1250 microns.

The elongated members can be formed from various materials so long as they are sufficiently stiff to provide the desired stimulatory effect. The materials can comprise metal or polymeric materials. By way of example, the metal can be stainless steel and the polymer can be at least one of nylon, polyester, polybutylene terephthalate (PBT), polyphenylene sulfide (PPS), and fluorinated polymers.

In some embodiments, at least one of the elongated flexible members bends upon application of a force in a range of about 0.05 milliNewtons (mN) to about 3000 mN thereto, where the force is applied normal to at least one of a proximal end and a distal end of said member. In some embodiments, at least one of the elongated flexible members bends upon application of a pressure in a range of about $4.1 \times 10^{-8}$ (N/mm$^2$) to about $6.1 \times 10^3$ (N/mm$^2$) thereto, wherein the pressure is applied normal to at least one of a proximal end or a distal end of the flexible member. Such a pressure is an average pressure that can be applied to the distal ends of the elongated flexible members parallel to their lengths to cause the flexible members to buckle. In some embodiments, the peak pressure applied to the patient's skin during treatment can be, for example, in a range of about $4.1 \times 10-8$ (N/mm$^2$) to about $6 \times 10^5$ (N/mm$^2$).

In some embodiments, at least one, and preferably all of, the elongated flexible members are configured such that upon bending, a linear distance between a proximal end and a distal end of flexible member is reduced between about 0.1 mm and about 10 mm. The surface density of said elongated flexible members can range from about 0.2 filaments per mm$^2$ to about 4 filaments per mm$^2$. In some embodiments, the number of the elongated flexible members can range from 1 to 10,000 members, or between 1 and 1000 member, or between 1 and 100 members, or between 10 and 50 members, or between 20 and 40 members or about 35 members.

In some embodiments, the motor coupled via a linkage to the base element can move the base element to and fro at a rate in a range from about 1 Hz to about 1000 Hz, or from about 5 Hz to about 500 Hz, or from about 20 Hz to about 100 Hz, or in a range of about 20 Hz to about 40 Hz.

The skin reference element and the elongated skin-contacting members can be arranged concentrically. In some embodiments, the elongated flexible members at least partially surround the skin reference element. In other embodiments, the skin reference element can at least partially surround the elongated flexible members. In other embodiments, two skin reference elements can be employed, one within a ring (or partial ring) of elongate members and one outside the ring (or partial ring) of elongate members.

In some embodiments, the plurality of elongated flexible members can include at least two subsets, where the flexible members in one subset differ in at least one property relative to the flexible members in the other subset. For example, the elongated flexible members in one subset can have a different length and/or a different shape relative to the elongated flexible members in the other subset.

In some embodiments, the base element can include a plurality of elements that are configured for independent movement so that different subsets of the elongated flexible members coupled to those elements can be moved independently.

In some embodiments, the base element can be rotatable about a longitudinal axis thereof so as to provide radial movement of said elongated flexible members. The elongated members can also be induced to vibrate during skin contact to enhance the stimulatory effect.

In a related aspect, a disposable cartridge for a controlled stimulation device is disclosed, which includes a base element having a plurality of elongated flexible members, where the base element is configured to removably engage with a skin treatment device having at least one skin reference element with a distal end that defines a skin surface plane when placed in contact with a region of skin to be treated. The base element is movable such that distal ends of elongated members can move between at least two positions, one position being a stowed position at or behind the distal end of the skin reference element and the other position being a deployed position in which the distal ends of the elongated members protrude to contact or penetrate the skin region. In some embodiments, the two positions are separated by a distance in a range of about 1 mm to about 15 mm, e.g., in a range of about 0.25 mm to about 0.75 mm. In some embodiments, in the deployed position, the distal ends of the elongated members protrude distally beyond the distal end of the skin reference element to contact or penetrate the skin region.

The treatment device can include an energy source for generating treatment energy and each of the base element and the skin reference element can include an aperture to allow passage of said treatment energy to the skin. In some embodiments, the energy source can be a light source. In other embodiments, the energy source can be a radiofrequency source. Yet, in other embodiments, a combination of a light source and radiofrequency source can be employed. In other embodiments, the treatment device can be a mechanical treatment device, e.g., one that includes a plurality of needles that can be inserted into a patient's skin.

In some embodiments, the cartridge further comprises a mount that is coupled to the base element such that the distal ends of elongated members can move between said stowed position and said deployed position. In some embodiments, the cartridge is configured to couple to the treatment device, e.g., as a sleeve around a handpiece. In some embodiments, the cartridge can further include a motor that is coupled to the base element via a linkage for inducing movement of the base element.

In some embodiments, the motor and the linkage can be removably and replaceably coupled to an outer surface of the body of the treatment device. The linkage can impart axial motion to the base element. In some embodiments, the linkage can impart a rotary motion to the base element. In some embodiments, the linkage can include a reciprocating drive shaft. In some embodiments, the linkage can include a cam, e.g., a cylindrical/axial or tangent cam, that is coupled to a drive shaft, where the drive shaft is in turn coupled to the base element.

In some embodiments, the motor can be configured to cause periodic movement of said base element at a rate in a range from about 1 Hz to about 1000 Hz, or from about 5 Hz to about 500 Hz, or from about 20 Hz to about 100 Hz, or from about 20 Hz to about 40 Hz.

The distal ends of the elongated members can have a variety of different shapes. For example, the shape of the distal ends can be at least one of a round point, a star point, a cross point, a tapered face, a beveled face (e.g., beveled at an angle between 30 and 60 degrees, preferably about 45 degrees), a multi-facet face, and/or a conical, spherical, elliptical, or hyper-elliptical shape, without or without grooves, e.g., micro-ridges or micro-lines. In some embodiments, the distal ends of the elongated flexible members can have a stop, e.g., in form of a collar, that limits the penetration depth of the distal ends into the patient's skin. Further, in some embodiments, Further, in some embodiments, the distal ends can have a shape that can facilitate causing depression into the skin upon contact without penetrating the skin. For example, in some such embodiments, the distal ends can have a substantially flat end.

In some embodiments, the plurality of the elongated flexible members of the cartridge can have a length in a range of about 0.05 mm to about 150 mm. Further, in some embodiments, the plurality of elongated flexible members can have a cross-sectional area in a range of about 0.02 mm$^2$ to about 20 mm$^2$. In some embodiments, the plurality of elongated flexible members of the cartridge are substantially cylindrical. In some such embodiments, the cylindrical members can have a diameter in a range of about 25 microns to about 1250 microns, e.g., in a range of about 50 microns to 200 microns. In some embodiments, the elongated flexible members of the cartridge can include at least one metal and a polymer. In some embodiments, the metal can be stainless steel and the polymer can be any of nylon, polyester, polybutylene terephthalate (PBT), polyphenylene sulfide (PPS), and fluorinated polymers.

In some embodiments, at least one of the elongated flexible members of the cartridge bends upon application of a force in a range of about 0.05 mN to about 300 mN thereto, where the force is applied normal to at least one of a proximal end and a distal end of said member. In some embodiments, at least one of the elongated flexible members bends upon application of a pressure in a range of about $4.1 \times 10^{-8}$ (N/mm$^2$) to about $6.1 \times 10^3$ (N/mm$^2$) thereto, wherein the pressure is applied normal to at least one of a proximal end or a distal end of the flexible member. Such a pressure is an average pressure that can be applied to the distal ends of the elongated flexible members parallel to their lengths to cause the flexible members to buckle. In some embodiments, the peak pressure applied to the patient's skin during treatment can be, for example, in a range of about $4.1 \times 10^{-8}$ (N/mm$^2$) to about $6 \times 10^5$ (N/mm$^2$). In some embodiments, the elongated flexible members are configured such that upon bending, a linear distance between a proximal end and a distal end of the flexible member is reduced between about 0.1 mm to about 10 mm.

In some embodiments, a surface density of the elongated flexible members can be in a range of about 0.2 filaments per mm$^2$ to about 4 filaments per mm$^2$. The number of the flexible elements of the cartridge can range from 1 to about 10,000 members, or between about 10 and about 1000 members or 1 and about 100, or in a range about 35 and about 50 members. In some embodiments of the above cartridge, the elongated flexible members at least partially surround said skin reference element. In other embodiments, the skin reference element can at least partially surround the elongated flexible members. In some embodiments, the elongated flexible members are arranged to at least partially surround a treatment region.

In some embodiments of the above cartridge, the plurality of elongated flexible members include at least two subsets, where the flexible members in one subset differ in at least one property relative to the flexible members in the other subset. For example, the flexible members in the two subsets can have different lengths, cross-sectional areas, shapes, etc. For example, in some embodiments, the distal ends of the elongated flexible members in one subset can have a different shape relative to the distal ends of the elongated flexible members in the other subset.

In some embodiments, the base element can include a plurality of elements that are configured for independent movement so that different subsets of the elongated flexible members can be moved independently. Further, in some such embodiments, the independently movable elements can be longitudinally movable so as to engage and disengage the distal ends of the flexible members with the skin along an axial direction. Alternatively, the independently movable elements can be rotatable about a longitudinal axis thereof so as to provide radial movement of the elongated flexible members.

In another aspect, a method of controlled stimulation during skin treatment is disclosed, which include contacting a region of skin with at least one skin reference element having a distal end that defines a skin surface plane, and deploying a plurality of elongated flexible members to repeatedly contact or penetrate the skin, the plurality of elongated members being attached to a base element that is movable such that the distal ends of elongated members can move between at least two positions, one position being a stowed position at or behind the distal end of the skin reference member and the other position being a deployed position in which the distal ends of the elongated members protrude to contact or penetrate the skin region. In some embodiments, in the deployed position, the distal ends of the elongated members protrude distally beyond the distal end of the skin reference element to contact or penetrate the skin.

In some embodiments, the movement of the distal ends of the elongated flexible members is repetitive, e.g., oscillatory, motion at a frequency in the range of about 1 Hz to about 1000 Hz or between about 5 Hz and about 500 Hz, or between about 10 Hz and about 200 Hz, or between about 20 Hz and about 100 Hz, or between 20 Hz and about 40 Hz, or at a rate of about 31 Hz. Further in some embodiments, the movement of the distal ends of the elongated flexible members is an axial oscillatory motion. In other embodiments, the movement of the distal ends of the elongated flexible members is a rotary motion or a vibratory motion, or a combination of axial, rotational and/or vibratory motions.

In a related aspect, a dermatological treatment device is disclosed, which comprises a handpiece having an energy source for generating energy for skin treatment, a controlled stimulation device for reducing pain perception during the treatment, said controlled stimulation device being configured for removable and replaceable coupling to said handpiece. The controlled stimulation device comprises at least one skin reference element having a distal end that defines a skin surface plane when placed in contact with a region of skin to be treated, a base element movable relative to the skin reference element, and one or more elongated (and preferably flexible) members coupled to the base plate, such that distal ends of the elongated flexible members can move between at least two positions, one position being a stowed position at or behind the distal end of the skin reference element and the other position being a deployed position in which the distal ends of the elongated members protrude to contact or penetrate the skin region. In some embodiments, the distal ends of the elongated members protrude distally beyond the distal end of the skin reference element to contact or penetrate the skin region.

In some embodiments, the treatment device can include a controller for controlling and coordinating activation of said energy source and said controlled stimulation device. In some embodiments, the energy source is a light energy source. In other embodiments, the energy source is a radiofrequency (RF) energy source. In other embodiments, the energy source is a mechanical source.

In some embodiments, a motor is disposed in any of said handpiece and the controlled stimulation device, where the motor is coupled via a linkage to the base element to induce movement thereof. In some embodiments, the motor is disposed in a sleeve that is configured for removable and replaceable coupling to the handpiece.

Another example of a controlled stimulation device in accordance with this disclosure includes a base element, a surface plate disposed longitudinally distally of the base element, the surface plate comprising a distal face, a plurality of elongated flexible members coupled to the base element, each of the plurality of flexible members comprising a proximal end and a distal end, and means for oscillating at least one of the base element and the flexible members, wherein the distal ends of the flexible members oscillate distally and proximally of the distal face of the surface plate.

The distal ends of the plurality of elongated flexible members can be shaped to facilitate the counterstimulatory effect. For example, the skin-contacting end can comprise at least one of a round point, a star point, a cross point, a tapered face, a beveled face (e.g., beveled at an angle between 30 and 60 degrees, preferably about 45 degrees), a multi-facet face, and/or a conical, spherical, elliptical, or hyper-elliptical shape, without or without grooves, e.g., micro-ridges or micro-lines.

The length of the elongated flexible members can be uniform or can vary. The length can range between about 0.05 mm and about 150 mm. By way of example, the individual elongated members can have a cross sectional area between about 0.002 mm$^2$ and about 20 mm$^2$, or a diameter between about 25 μm and about 200 μm.

The plurality of elongated flexible members can comprise at least one of a metal such as for example, stainless steel or at least one polymer such as, for example, nylon, polyester, polybutylene terephthalate (PBT), polyphenylene sulfide (PPS), and fluorinated polymers.

The elongated members are preferably flexible and can bend upon application of a force between about 0.05 milliNewtons (mN) and about 3000 mN per element, as measured when such a force is normal to at least one of the proximal end and the distal end of the flexible members. In some embodiments, at least one of the elongated flexible members bends upon application of a pressure in a range of about $4.1 \times 10^{-8}$ (N/mm$^2$) to about $6.1 \times 10^3$ (N/mm$^2$) thereto, wherein the pressure is applied normal to at least one of a proximal end or a distal end of the flexible member. Such a pressure is an average pressure that can be applied to the distal ends of the elongated flexible members parallel to their lengths to cause the flexible members to buckle. In some embodiments, the peak pressure applied to the patient's skin during treatment can be, for example, in a range of about $4.1 \times 10^{-8}$ (N/mm$^2$) to about $6 \times 10^5$ (N/mm$^2$).

In some embodiments, the elongated members can be disposed in one or more rings or partial rings. A plurality of elongated members is preferably deployed to contact a skin area such that the density of members is between about 0.2 members (filaments) per mm$^2$ and about 4.0 members (filaments) per mm$^2$. By way of example, the number of elongated members can range from 1 to about 10,000 members, or between 1 and about 1000, or between about 10 and 100 members, or about 35 to about 50 members.

The elongated members are preferably flexible and can bend such that a linear distance between the proximal end and the distal end of the flexible members reduces upon application of skin resistance to the distal end of the flexible members. For example, the linear distance between the proximal end and the distal end of the flexible members can decrease between about 0.1 mm and about 10 mm upon application of a pressure in a range of about $4.1 \times 10^{-8}$ (N/mm$^2$) to about $6.1 \times 10^3$ (N/mm$^2$) thereto, as measured when the pressure is applied normal to at least one of a proximal end or a distal end of the flexible member.

Preferably, the elongated members are driven to repeatedly move between a retracted and an extended (deployed) position. The driver for such a motion can be a drive shaft coupled to the base element that is driven to provide an oscillating motion, for example, by a motor and a cam coupled to the drive shaft. By way of example, the cam can comprise a cam slot configured to continuously oscillate or to maintain the flexible members at certain axial positions for a predetermined period of time. In certain embodiments, the elongated members can be driven to oscillate at a rate of between about 1 Hz to about 1000 Hz or between about 5 Hz and about 200 Hz, or between about 10 Hz and about 100 Hz, or between about 20 Hz and about 40 Hz, or at a rate of about 23 Hz.

In certain embodiments it can be preferable for the elongated members to extend a predetermined distance distally from the distal face of the surface plate when they are at their most extended or deployed position, e.g., contacting or penetrating the skin. This fully extended distance can range, for example, from about 0.1 mm to about 15 mm or between 0.25 mm and 7.5 mm.

In some embodiments, the elongated flexible members can bend a second predetermined distance upon application of a force to at least one of the proximal end and the distal ends of the flexible members after the flexible members oscillate distally of the distal face of the surface plate the predetermined distance, wherein the second predetermined distance is less than the first predetermined distance. The elongated flexible members can bend such that a linear distance between the proximal end and the distal end of the flexible members reduces upon application of pressure to the distal end of the flexible members.

The distal surface of the skin surface reference member can have a ring-shaped or partial ring shaped skin-contacting face. This skin surface plate can be concentric with the one or more rings (or partial rings) of the elongated members and can be disposed radially inward of the elongated members or radially outside of the elongated members. In certain embodiments, both a radially inner skin surface reference member and radially outer skin surface reference member can be employed.

The plurality of elongated flexible members can include a first set or subset of the plurality of elongated flexible members and a second set or subset of elongated flexible members, wherein the first set of elongated flexible members differs from the second set of the elongated flexible members. For example, the ends of the first subset of elongated flexible members can extend distally beyond the ends of the second set of elongated flexible members, wherein both sets of elongated flexible members are coupled to the base element. In certain embodiments, the first subset of elongated flexible members can extend distally beyond the ends of the second subset of elongated flexible members due to placement of the first subset on a raised portion of the base element. Alternatively, the first subset of elongated flexible members can be longer (or shorter) in length than the second subset of elongated flexible members. The distal ends of the first subset or second subset of the elongated flexible members can comprise at least one of a flat end, round point, star point, cross point, tapered faced, bevel faced, multi-faced, conical, spherical, elliptical, hyper-elliptical, line contact, micro-ridge and micro-line shape, and/or wherein the diameter, cross sectional shape, flexibility, bend resistance, sharpness, and/or rigidity of the materials used to form the first set of the elongated flexible members differ from those used to form the second set of the elongated flexible members.

In certain embodiments, the surface plate is disposed longitudinally distally of the base element, and the first set of a plurality of elongated flexible members are coupled to the base element and a second set of the plurality of shorter elongated flexible members are coupled to the base element, wherein the first set of elongated flexible members extend distally beyond the ends of the second elongated flexible members relative to the base element. The distal ends of the shorter set of the elongated flexible members can comprise a round point, spherical, elliptical, line contact, micro-ridge and micro-line shape, and/or wherein the diameter, cross sectional shape, flexibility, bend resistance, dullness, and/or rigidity of the materials used to form the shorter set of the elongated flexible members are intended to generate sensory tactile vibration, wherein the difference in height or length of the first and shorter elements limit the exposure of the first set and sufficient to limit the bending properties of the longer elements thereby acting in a mechanical fashion like a surface plate, while the first and second sets of elongated flexible elements oscillate relative to the epithelium and/or skin surface.

An example of a treatment device in accordance with this disclosure includes one or more emitters capable of emitting electromagnetic energy, and the controlled stimulation device of any of the preceding paragraphs. Another example of another treatment device in accordance with this disclosure includes one or more needles (hollow or solid), and a controlled stimulation device of any of the preceding paragraphs. Treatment systems (e.g., treatment devices used in conjunction with the controlled stimulation devices of the disclosure) can further comprise a controller for controlling and coordinating activation of the treatment device and the controlled stimulation device of any of the preceding paragraphs.

In one aspect, a treatment device is disclosed, which include a movable base element to which a plurality of needles are coupled, where the needles are configured for penetration into a patient's skin to provide a treatment. A plurality of elongated flexible members are also coupled to the base element. The base element is movable between a stowed position and a deployed position, where in the deployed position, the needles can penetrate the skin and the flexible elongated elements can contact or penetrate the skin. In some embodiments, the based element can be repetitively moved (e.g., it can be oscillated) such that the contact or penetration of the elongated flexible elements with the patient's skin can reduce discomfort and pain that would be otherwise triggered by penetration of the needles into the skin. In some embodiments, the needles can have a sharp end to facilitate their penetration into the skin. The shapes of the elongated flexible members can be any of the shapes disclosed herein. In some embodiments, the device can include at least one skin reference element having a distal end that defines a skin surface plane when placed in contact with a region of skin to be treated. In some embodiments, in the stowed position, the base element can be disposed behind the distal end of the skin surface element and can protrude distally beyond the distal end of the skin reference element, when in a deployed position.

An example of a method of using a device to treat a patient, wherein the target region is skin, e.g., the epithelium or underlying skin tissue, the method includes providing a device, wherein the device comprises a base element, a skin surface reference member disposed longitudinally distally of the base element, the surface plate comprising a distal face, one or more elongated flexible members coupled to the base element, each of the plurality of elongated flexible members comprising a proximal end and a distal end, and a driver for oscillating the base elements, wherein the distal ends of the flexible members move distally and proximally of the distal face of the surface plate, placing the surface plate adjacent to, or in contact with, the epithelium of the patient, and activating the driver to move at least one of the base element and the flexible members, whereupon activation, the flexible members move to engage and disengage the skin of the patient.

The methods of the present disclosure can further include the step of varying the position of the elongated flexible members to engage and disengage a patient's skin at a rate of between about 1 Hz and about 1000 Hz. The flexible members are preferably elongated and are driven to move along to and fro along their longitudinal axes. Preferably, a target region of skin has a substantially planar surface and the flexible members move to and fro in a direction normal to the skin surface while the user maintains placement of the skin surface reference element adjacent to the patient's epithelium. The flexible members can also move or oscillate to engage and disengage the skin of the patient while moving the device along the skin of the patient. The flexible members can also bend upon engaging the skin of the patient and straighten upon disengaging the skin of the patient.

In certain methods according to the disclosure, the flexible members bend upon application of a force between about 0.05 milliNewtons (mN) and about 3000 mN per flexible member. The force can be applied and/or measured normal to at least one of the proximal end and the distal ends of the flexible members. Alternatively, the flexible members can bend upon application of a pressure between about $4.1 \times 10^{-8}$ (N/mm$^2$) to about $6.1 \times 10^3$ (N/mm$^2$), wherein the pressure is applied and/or measured normal to at least one of the proximal end and the distal ends of the flexible members.

The method can further comprise moving the base element and the flexible members in a lateral direction or a rotational direction normal to the direction of the longitudinal axis of the elongated flexible members and normal to the surface of the skin or tissue being treated, or by vibrating the members thereby varying the position on the skin or tissue where the elongated flexible members impact the skin or tissue during oscillation of the flexible members in a direction distally and proximally of the distal face of the surface plate and potentially enhancing the ability of the device to stimulate or elicit the desired effect on the skin or tissue. In some embodiments, such rotational or vibratory motion can be in addition to oscillating the flexible members in a direction distally and proximally of the distal face of the surface plate. Movement of the base element and the flexible members in a lateral direction or a rotational direction normal to the direction of the longitudinal axes of the flexible members and normal to the surface of the skin or tissue being treated minimizes and/or reduces and/or prevents the distal ends of elements repeatedly contacting the tissue in the exact, same or similar location over, so as to prevent habituation or otherwise more effectively condition the tissue or its sensory aspects of skin or tissue; by providing a rotational or a lateral motion (perpendicular to up and down motion of the elongated flexible members) the location of the skin and/or tissue that the elongated flexible members contact will vary and thereby further enhance the device's effect, particularly when the device is in located for a period of time on a particular area of the skin or tissue in a repetitive and/or stamping fashion and not subject to continuous movement across the surface by the operator or patient.

In another method in accordance with this disclosure, the method can include providing a controlled stimulation device, wherein the controlled stimulation device comprises a base element, a surface plate disposed longitudinally distally of the base element, the surface plate comprising a distal face, a plurality of elongated flexible members coupled to the base element, each of the plurality of flexible members comprising a proximal end and a distal end, and a driver for oscillating the base element and the flexible members, wherein the distal ends of the flexible members oscillate distally and proximally of the distal face of the surface plate, placing the surface plate adjacent the skin of the patient, activating the means for oscillating the base element and the flexible members, whereupon activation, the flexible members oscillate to engage and disengage the skin of the patient, while applying treatment to the patient.

The method can further include the step of applying treatment to the skin comprising using a treatment device. The treatment can be light-based and the treatment device can comprise a laser or light-emitted energy applicator. Alternatively, or in addition, the treatment can employ an electric field or current and the treatment device can comprise an array of needles (e.g., micro-needles) or other applicators capable of emitting radiofrequency (RF) energy.

In any of these treatment methods, the flexible members can radially surround at least a portion of treatment device and the surface plate can be radially disposed (inside or outside) relative to the flexible members. The flexible members can each have a longitudinal axis, along which the flexible members move to and fro, e.g., oscillate, in a direction substantially normal to the skin of the patient.

The methods can further include a step of moving the device along the skin of the patient while maintaining placement of the surface plate adjacent the patient's skin. The flexible members can be activated to engage and disengage the skin of the patient while moving the device along the skin of the patient.

For example, the flexible members can oscillate while the treatment device applies treatment. The methods can further comprise a step of controlling timing of oscillation of the flexible members and application of treatment in a phased-controlled manner.

The method of any of the preceding paragraphs can further comprise a step of controlling the motion of the flexible members to engage the skin of the patient prior to applying treatment, or engaging the skin of the patient substantially simultaneously during application of treatment, or subsequent to applying treatment.

Methods according to the disclosure can further include controlling the elongated flexible members to bend in order to condition the skin and such methods can be adjusted to optimize effects on tissue or the patient's sensory system particular to the one or more target areas of treatment. In some embodiments, the purpose of the method includes enhancing the vascularity of the tissue and in such case the filament diameter, stiffness, length, tip shape etc. can be adjusted and/or varied to a greater stiffness range that would otherwise be used if the intent were to evoke or desensitize the sensory apparatus.

The methods of any of the preceding paragraphs can further include controlling the extent of penetration of elongated members into tissue is usefully employed so as to stimulate the body's natural healing response to rejuvenate skin or other tissue. The devices of the present invention have distinct advantages relative to conventional micro-needling devices, such as the ability to manipulate and/or control the extent of penetration by optimizing the selection of filament properties via their inherent bending properties. This approach has advantages over micro-needling devices that employ stiffer metal needles.

An example of another device in accordance with this disclosure for controlled stimulation, includes a base element, a plurality of elongated flexible members coupled to the base element, each of the plurality of flexible members comprising a proximal end and a distal end, and means for oscillating the base element and the flexible members, wherein the distal ends of the flexible members oscillate distally and proximally.

In such devices, the distal ends of the plurality of elongated flexible members comprise at least one of a round point, star point, cross point, tapered faced, bevel faced a beveled face, (e.g., beveled at an angle between 30 and 60 degrees, preferably about 45 degrees), multi-faced, conical, spherical, elliptical, hyper-elliptical, line contact, micro-ridge and micro-line shape. The plurality of elongated flexible members comprise a length, and the length can be between about 0.05 mm and about 150 mm. The plurality of elongated flexible members comprise a cross sectional area, and the cross sectional area is between about $0.002$ mm$^2$ and about 20 mm$^2$ and/or a diameter between about 25 μm and about 1250 μm.

The elongated flexible members can bend upon application of a force between about 0.05 milliNewtons (mN) and about 3000 mN per element, wherein the force is applied and/or measured normal to at least one of the proximal end and the distal ends of the flexible members. Alternatively, the elongated flexible members can bend upon application of a pressure between about $4.1 \times 10^{-8}$ (N/mm$^2$) to about $6.1 \times 10^3$ (N/mm$^2$), wherein the pressure is applied and/or measured normal to at least one of the proximal end and the distal ends of the flexible members.

In the devices of any of the preceding paragraphs, the density of flexible members can range, for example, from about 0.2 filaments per mm$^2$ to about 4.0 filaments per mm$^2$ and the elongated flexible members can bend such that a linear distance between the proximal end and the distal end of the flexible members reduces upon application of resistance to the distal end of the flexible members. When bending the linear distance between the proximal end and the distal end of the flexible members reduces between about 0.1 mm and about 10 mm.

In the devices of any of the preceding paragraphs, the mechanism for repetitively moving the base element and the flexible members can comprise a drive shaft coupled to the base element, and can further comprise a cam coupled to the drive shaft and a motor coupled to at least one of the cam and the drive shaft. The cam can also comprise a cam slot. The cam slot can be configured to maintain the flexible members at an axial position for a predetermined period of time.

The present disclosure further encompasses the devices of any of the preceding paragraphs, wherein the driver for moving at least one of the base element and the flexible members oscillates the at least one of the base element and the flexible members at a rate of between about 1 Hz and about 1000 Hz or between about 5 Hz and about 200 Hz, or between about 10 Hz and about 100 Hz, or between about 20 Hz and about 40 Hz.

Another example of a treatment device of the present disclosure includes one or more microneedles and the controlled stimulation device of any of the preceding paragraphs. Such a treatment device can further comprise a controller for controlling and coordinating activation of the one or more microneedles and the controlled stimulation device of any of the preceding paragraphs. In such devices, the one or more microneedles can be disposed radially inward of the plurality of elongated flexible members.

Another example of a treatment device of the present disclosure includes one or more emitters capable of emitting electromagnetic energy, and the controlled stimulation device of any of the preceding paragraphs. Again, the treatment device can comprise a controller for controlling and coordinating activation of the one or more emitters and the controlled stimulation device of any of the preceding paragraphs and the flexible members can be disposed radially outward of the electromagnetic energy emitted by the one or more emitters.

Another example of a method of using a device to treat a patient includes providing a device, wherein the device comprises, a base element, a plurality of elongated flexible members coupled to the base element, each of the plurality of flexible members comprising a proximal end and a distal end, and a driver for oscillating the base element and the flexible members, wherein the distal ends of the flexible members oscillate distally and proximally, placing the distal ends of the plurality of flexible members adjacent the skin of the patient, and activating the means for oscillating at least one of the base element and the flexible members, whereupon activation, the flexible members oscillate to engage and disengage the skin of the patient.

Another example of a method of using a controlled stimulation device to treat a patient of the preceding paragraph includes providing a controlled stimulation device, wherein the controlled stimulation device comprises a base element, a plurality of elongated flexible members coupled to the base element, each of the plurality of flexible members comprising a proximal end and a distal end, and means for oscillating the base element and the flexible members, wherein the distal ends of the flexible members oscillate distally and proximally, placing the distal ends of the elongated flexible members adjacent the skin of the patient, activating the means for oscillating the base element and the flexible members, whereupon activation, the flexible members oscillate to engage and disengage the skin of the patient, and applying treatment to the skin of the patient.

The methods of the present disclosure can comprise the step of applying treatment to the skin comprising using a treatment device, for further example, with an array of microneedles. The array of microneedles are capable of emitting radiofrequency energy. Alternatively, the treatment device comprises one or more electromagnetic energy emitters.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

Figure 1:
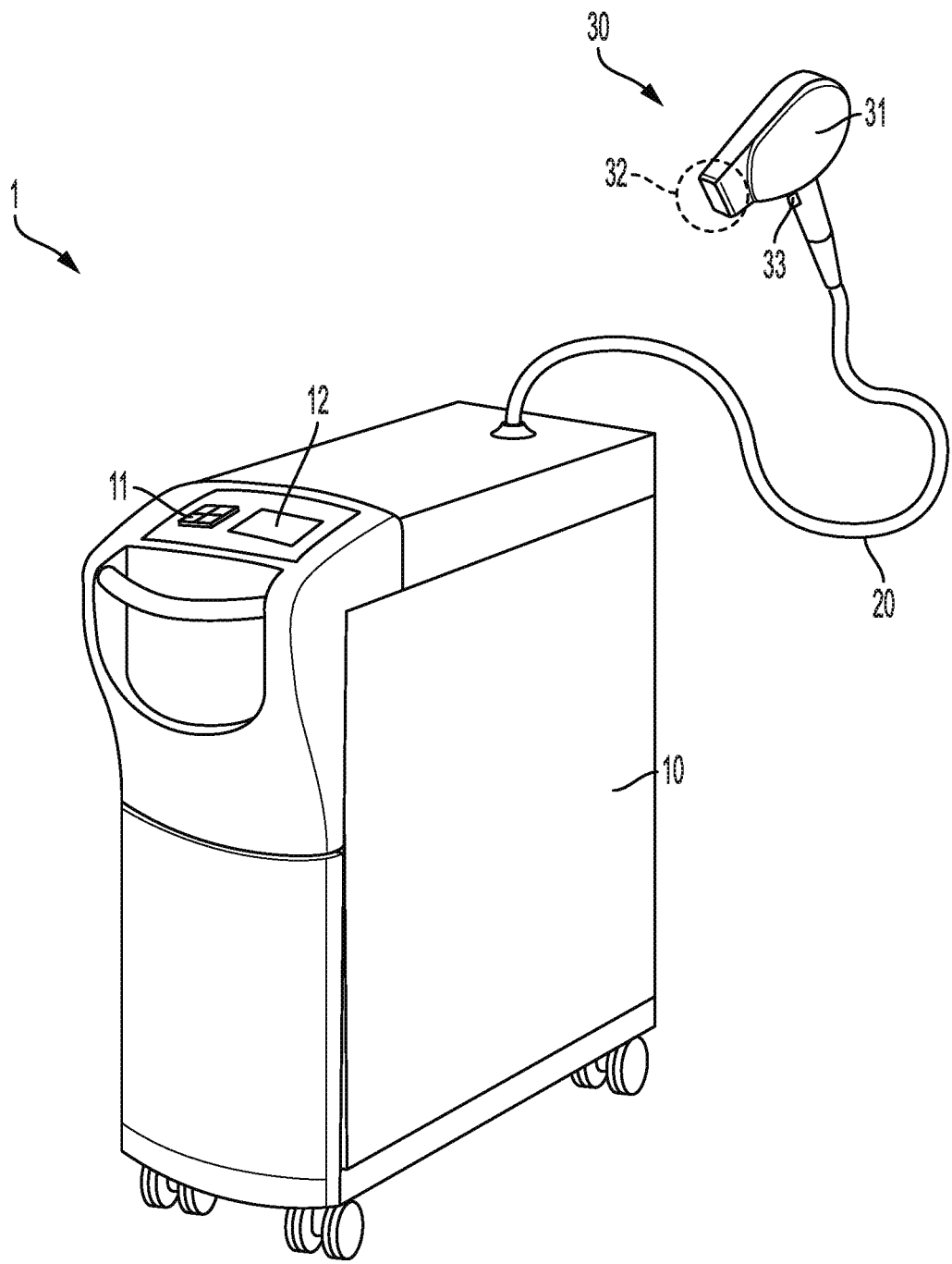
FIG. 1 illustrates a light treatment device or system.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1-X_n$, $Y_1-Y_m$, and $Z_1-Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "computer-readable medium" as used herein refers to any storage and/or transmission medium that participate in providing instructions to a processor for execution. Such a medium is commonly tangible and non-transient and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

The term "logic" or " "control logic" as used herein may include software and/or firmware executing on one or more programmable processors, application-specific integrated circuits (ASICs), field-programmable gate arrays (FPGAs), digital signal processors (DSPs), hardwired logic, or combinations thereof. Therefore, in accordance with the embodiments, various logic may be implemented in any appropriate fashion on and/or in conjunction with computer-readable medium and would remain in accordance with the embodiments herein disclosed.

The terms "flexible member," "flexible elongate member," "brush," and "filament" are used interchangeably herein.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "skin" denoted a target region to which treatment is applied, including without limitation the epidermis, epithelium, dermis and underlying tissue. The term "skin surface plane" as used herein is intended to encompass the region of skin to which treatment energy is applied. It need not be strictly "planar." Rather it denotes a relatively flat skin surface region onto which the controlled stimulation devices of the present invention can be applied. The phase "surface density" as applied to the elongated (or flexible elongated) members refers the number of elongated members per unit area, e.g. a unit area of the surface of the base element to which the members are coupled.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The present disclosure is also directed to a controlled stimulation device that can be used either alone or in conjunction with a treatment device. Examples of treatment devices include aesthetic, surgical, and medical devices, including, but not limited to, energy-emitting devices, including, but not limited to, light-emitting devices (e.g., lasers and high powered lamps) and devices applying different treatment modalities (e.g., radio-frequency emitting micro-pad or micro-needle devices). Such treatment devices can be used for hair reduction, hair removal, treating pigmented lesions, reducing wrinkles and scars in skin, skin rejuvenation, treating vascular lesions (e.g., birthmarks, rosacea, spider veins, varicose veins, telangiectasias, etc.), applying or removing tattoos and treating melasma. Examples of laser treatment devices include the Clarity™ dual wavelength alexandrite & Nd:YAG laser, and LaseMD™ thulium laser which are two of the aesthetic lasers commercialized by Lutronic Corporation located in South Korea. Illustrations and descriptions of aesthetic lasers are included in U.S. Publication No. 2009/0105696 A1 having application Ser. No. 12/280,460 published Apr. 23, 2009 and PCT Publication No. WO 2017/164430 A1 having application serial no. PCT/KR2016/002882 published Sep. 28, 2017 both of which are hereby incorporated by reference for all they teach and for all purposes. Further examples of treatment devices are the Lutronic Genius™ and Infini™ radio frequency (RF) micro-needling devices, which are also commercialized by Lutronic Corporation. Illustrations and descriptions of such treatment devices can also be found in U.S. Publication No. 2014/0194789 A1 having application Ser. No. 14/234,864 published Jul. 10, 2014 and U.S. Publication No. 2014/0358200 A1 having application Ser. No. 14/360,494 published Dec. 4, 2014 both of which are hereby incorporated by reference for all they teach and for all purposes.

Referring to FIG. 1 of the present application, which is similar to FIG. 1 of PCT Publication No. WO 2017/164430 A1, there is a shown a light treatment device or system 1 comprising a console 10, a hand-piece 30 and a connecting unit 20. The console 10 may comprise control electronics, power supply and one or more light sources (e.g., one or more lasers) of the light therapy device. For example, the console may include both a 755 nm wavelength (Alexandrite source) and 1064 nm wavelength (Nd:YAG source). The console 10 is typically connected to an external power supply, e.g., 110 or 240 volt alternating current by a plug (not shown). The console may have a control panel 11 and a display 12 to manipulate and display, respectively, the treatment information for the procedure. Connection unit 20 is configured to couple and/or connect the body 10 and the hand-piece 30. The connection unit 20 may comprise a conduit for delivering the light to the hand piece 30, such as one or more light guides (e.g., optical fibers). The connection unit may be flexible to allow the position of the hand-piece 30 to be adjusted by the operator. Hand-piece 30 is configured to be gripped by the operator and movable into the treatment position where the operator will then activate it to emit irradiating light to the treatment area. The hand-piece 30 may also include the light source (e.g., lamp or laser). The hand-piece 30 may include a housing 31, a button/switch 33 and a light emitting portion 32. Upon placing the hand-piece 30 against a treatment site (e.g., patient's skin) and activating the switch 33 (often the operator also has to step on a foot switch, not shown), the light emitting portion 32 applies an irradiating light to the treatment site to effect treatment. Although FIG. 1 illustrates the hand-piece 30 as having a particular shape, it is intended that the hand-piece can also have alternate shapes. Particularly, the controlled stimulation devices of the present invention are adapted to couple to, or be integrated with, hand-piece 30.

Figure 2:
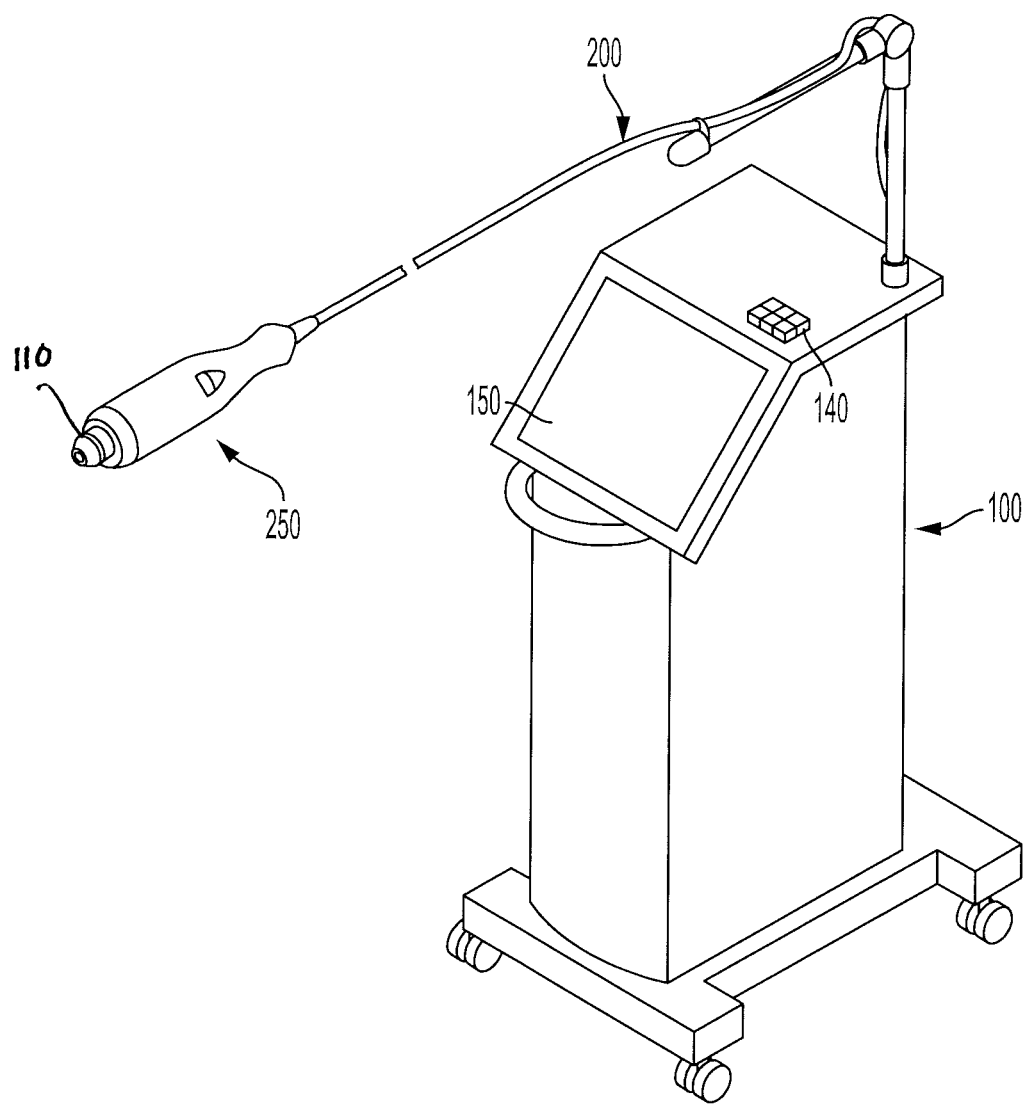
FIG. 2 illustrates a high-frequency radio-frequency (RF) microneedle treatment device.

Referring to FIG. 2 of the present application, which is similar to FIG. 1 of U.S. Publication No. 2014/0194789 A1, there is a shown a treatment apparatus that can emit high-frequency waves to provide treatment. The high-frequency treatment apparatus may comprise a console 100, a hand piece 250, and a cable 200 that connects the console 100 with the hand piece 250. The console 100 includes a power supply (not shown) and a high-frequency generator, such as an RF generator that produces RF energy, and often receives external power. The console 100 may include a control panel 140 and a display 150 to manipulate and display, respectively, the treatment information for the procedure. The hand piece 250 can include an electrode unit 310 (FIG. 3), which is typically electrically connected to the high-frequency wave generating unit of console 100. Again, the controlled stimulation devices of the present invention are adapted to couple to, or be integrated with, hand-piece 250.

The controlled stimulation devices disclosed herein can be used with other treatment devices, including but not limited to other types of mechanical and/or electromagnetic energy emitting medical devices. For example, other types of mechanical devices may include needle-based and non-needle based injections, oscillating needle insertion/retraction such as tattoo application devices, needling, dermabrasion, tweezing, plucking, etc., and such medical devices may be motor powered to provide automatic penetration into the epithelium, other layers of the skin or tissue beneath the skin. Additionally, other types of electromagnetic radiation emitting medical devices may include devices that provide for electrostimulation, include broadband light sources, etc.

Referring to FIGS. 3-9 there is shown an example of a controlled stimulation device 300 that may be integral with, removably coupled with, or separately used in conjunction with a treatment device, such as the light treatment device 1 of FIG. 1, particularly the hand-piece 30 of the light treatment device 1 high-frequency treatment apparatus 100 of FIG. 2, particularly the hand-piece 250 of high-frequency treatment apparatus that may include an array of microneedles 110. The controlled stimulation device 300 reduces the amount of pain that a patient will feel or experience during utilization of the treatment device, such as hand-piece 30 or 250, in comparison to utilization of hand-piece 30 or 250 without the controlled stimulation device 300. The controlled stimulation device 300 may comprise a housing 303, proximal end 310, and a distal end 315. Although it is not shown in FIGS. 3-9, the controlled stimulation device 300 may include a light emitting portion of a light treatment device or a high-frequency portion of a high-frequency treatment apparatus. As such, the distal end 315 of the controlled stimulation device 300 is considered the treatment end of the device because light or high-frequency energy is emitted from the distal end 315 of the device.

Disposed and/or included at or toward the distal end 315 of the controlled stimulation device 300 is a base element (or base ring) 305 and a skin surface reference element 340, which may also be referred to as a contact plate. The contact plate 340 is disposed distally of the base element 305. One or more elongate flexible members 325 are attached to the base element 305. For example, the base element 305 can have a proximal facing side and a distal facing side. In certain embodiments, a plurality of flexible elongated members 325, each having a proximal end 330 and a distal end 335, can be attached to base element 305 at their proximal ends and extend from the distal facing side of the base element 305. (In alternative embodiments, a single elongated member with or without protrusions can be employed to provide the counterstimulatory effect.)

The base element 305 can have an open or closed ring-like shape, such as a square, rectangular, circular, oval, ellipse, orbital, arch shaped (e.g., horseshoe shaped) plate viewed from one or both of the faces of the base element 305. In certain embodiments, the base element 305 has an opening though which the light or radio frequency energy is emitted from the distal end 315 of the device. The base element 305, which is disposed radially outward from the emitted light, therefore, partially or completely surrounds the light. Because the flexible members 325 are attached to base element 305 and extend from the distal facing side of the base element 305, the flexible members 325 are disposed radially outward from the emitted light and also partially or completely surround the path of the light beam during treatment.

The skin is composed of two main layers: the epidermis, made of closely packed epithelial cells, and the dermis, made of dense, irregular connective tissue that houses blood vessels, hair follicles, sweat glands, and other structures. Beneath the dermis lies the hypodermis, which is composed mainly of loose connective and fatty tissues. The controlled stimulation device 300 can be designed such that the flexible members 325 penetrate only the outermost layer(s) of the epidermis and do not penetrate the inner layers of the epidermis or dermis, thereby activating the nociceptors while minimizing the potential effects of direct injury to the skin and the sequela that results while inhibiting the potential amount of pain experienced by the patient resulting from the treatment device. In order to ensure that this penetration depth is accomplished, the selection of the flexible members' 325 material, length, diameter, circumference, cross-sectional area, tip shape can be important. Alternatively, the flexible members 325 can be designed by selection of material, size and shape, to penetrate more deeply into the epidermis and possibly the dermis to evoke a skin response that leads to extended or transient irritation and the sequela thereof. But, again, it may be preferable to generate the desirable therapeutic responses and effects while reducing the potential amount of pain experienced by the patient resulting from the treatment device. In applications designed to avoid irritation and/or prolonged erythema from their application, it is desirable that the flexible members 325 penetrate the skin a certain depth, such as about half the thickness of the epidermis or about 50 microns and then after achieving such depth, bend or buckle in order to activate nociceptors while minimizing the potential damage to the skin or underlying tissue.

Another important factor in activating the nociceptors while evoking minimal response from the skin or underlying tissue includes controlling the duration of time that the flexible members 325 are pressed against the skin. As discussed in more detail below, the flexible members 325 oscillate toward and away from the patient's skin, thereby applying varying pressure (and force). The flexible members 325 may continuously contact the patient's skin, but continuous contact may irritate the skin and/or lead to rapid adaptation of the nociceptor, thereby minimizing the therapeutic benefits of controlled stimulation. In many procedures, treatments involve application of pulses of energy in a stepwise fashion across the patient's skin. If the flexible members were pressed against and into the skin and remained in that position while the handpiece was moved to an adjacent location, then the tips of the flexible elements could scratch the skin surface causing excessive irritation and injury. Accordingly, it may be more desirable for the controlled stimulation device 300 to be designed such that the flexible members 325 oscillate in a first direction (which is normal to the skin) such that they contact (or penetrate) the skin and then oscillate in a second (opposite) direction (which is normal to the skin) such that the flexible members 325 no longer contact the skin.

In order to penetrate the epidermis or skin to the desirable depth and initiate the nociceptors, the distal ends (or tip) of the flexible members 325 may be designed to have at least one of the following shapes: a round point, star point, cross point, tapered faced, bevel faced, multi-faced face, conical tip, spherical face, elliptical face, hyper-elliptical face, line contact, one or more grooves (e.g., micro-ridges/micro-lines). While in some embodiments, the flexible elements contact the skin without penetrating the skin, in other embodiments, the flexible members penetrate the skin. In order to penetrate the skin (e.g., the epidermis) to the desirable depth and initiate the nociceptors, the flexible members 325 may be designed to have a particular length between about 0.05 mm and about 150 mm. For example, the length of the flexible members 325 may be between about 0.50 mm and about 125 mm, between about 1.00 mm and about 100 mm, between about 2.00 mm and about 90 mm, between about 3.00 mm and about 80 mm, between about 4.00 mm and about 70 mm, between about 4.50 mm and about 60 mm, between about 5.0 mm and about 50 mm, between about 6.00 mm and about 40 mm, between about 0.05 mm and about 5.0 mm, between about 0.10 mm and about 4.0 mm between about 0.10 mm and about 3.0 mm, between about 0.10 mm and about 2.0 mm, between about 0.10 mm and about 2.0 mm, between about 0.10 mm and about 1.0 mm, between about 0.10 mm and about 0.90 mm, between about 0.10 mm and about 0.80 mm between about 0.10 mm and about 0.70 mm, between about 0.10 mm and about 0.60 mm, between about 0.15 mm and about 0.50 mm, and between about 0.20 mm and 0.40 about mm, including any value or increment thereof.

In order to penetrate the skin to the desirable depth and initiate the nociceptors, the flexible members 325 may be designed to have a particular diameter between about 25 micrometers (microns, μm) and about 1250 μm. For example, the diameter of the flexible members 325 may be between about 50 μm and about 1100 μm, between about 75 μm and about 1000 μm, between about 100 μm and about 900 μm, between about 125 μm and about 800 μm, between about 150 μm and about 700 μm, between about 175 μm and about 600 μm, between about 200 μm and about 500 μm, between about 225 μm and about 450 mm, between about 250 μm and about 400 μm, between about 275 μm and about 400 μm, between about 300 μm and about 375 μm, including any value or increment thereof. One particular example of an increment may include 10 μm, such that upon the flexible members 325 having a diameter between about 50 μm and about 250 μm shall include a diameter of about 50 μm, 60

μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, and 250 μm.

In order to penetrate the skin to the desirable depth and initiate the nociceptors, the flexible members 325 may be designed to have a cross sectional area between about 0.002 mm$^2$ and about 20 mm$^2$. Additionally, the length of the flexible members 325 may be between about 0.003 mm$^2$ and 10 mm$^2$, between about 0.004 mm$^2$ and 5 mm$^2$, between about 0.008 mm$^2$ and 2 mm$^2$, between about 0.010 mm$^2$ and 1.5 mm$^2$, between about 0.015 mm$^2$ and 1.0 mm$^2$, between about 0.020 mm$^2$ and 0.9 mm$^2$, between about 0.030 mm$^2$ and 0.8 mm$^2$, between about 0.040 mm$^2$ and 0.6 mm$^2$, between about 0.070 mm$^2$ and 0.5 mm$^2$, between about 0.080 mm$^2$ and 0.4 mm$^2$ between about 0.090 mm$^2$ and 3 mm$^2$, between about 0.1 mm$^2$ and 2 mm$^2$, between about 1.1 mm$^2$ and 1.9 mm$^2$, between about 1.2 mm$^2$ and 1.8 mm$^2$, between about 1.3 mm$^2$ and 1.7 mm$^2$, between about 0.1.4 mm$^2$ and 1.6 mm$^2$, including any value or increment therebetween.

In order to penetrate the skin to the desirable depth and initiate the nociceptors and then after achieving such depth, bend or buckle in order to minimize the potential damage to the skin or underlying tissue, the flexible members 325 may be designed to allow for such bending and/or buckling upon application of a particular force between about 0.05 milliNewtons (mN) and about 3000 mN per element, wherein the force is measured upon application to at least one of the proximal end and the distal ends of the flexible members. For example, the flexible members may be designed to bend and/or buckle upon application of a force equal to between about 0.05 mN and about 3,000 mN, including any value or increment therebetween, such as about 0.08 mN, 0.20 mN, 0.40 mN, 0.70 mN, 1.6 mN, 3.9 mN, 5.9 mN, 9.8 mN, 13.7 mN, 19.6 mN, 39.2 mN, 58.8 mN, 78.4 mN, 98.0 mN, 147 mN, 255 mN, 588 mN, 980 mN, 1,760 mN and 1,940 mN, including any value or increment thereabout.

In some embodiments, the distal ends of the flexible members can have a shape that inhibits penetration of the distal ends into the patient's skin beyond a desired depth. For example, the distal ends can have a tapered shape with wider upper section relative to the tip that can restrict the penetration of the distal ends into the patient's skin beyond a desired depth.

In order to penetrate the skin to the desirable depth and initiate the nociceptors and then after achieving such depth, bend or buckle in order to minimize the potential damage to the skin or underlying tissue, the flexible members 325 may be designed to allow for such bending and/or buckling upon application of a particular pressure between about 2 grams-force per millimeter squared (g-f/mm$^2$) and about 3000 g/mm$^2$ per element, including any value or increment therebetween, wherein the pressure is measured upon application of force to at least one of the proximal end and the distal ends of the flexible members. For example, the flexible members may be designed to bend and/or buckle upon application of a pressure in a range of about 4.1×10$^{-8}$ (N/mm$^2$) to about 6.1×10$^3$ (N/mm$^2$), e.g., in a range of about 10$^{-3}$ (N/mm$^2$) to 1000 (N/mm$^2$), or in a range of about 10$^{-2}$ (N/mm$^2$) to about 100 (N/mm$^2$) thereto, wherein the pressure is applied normal to at least one of a proximal end or a distal end of the flexible member. Such a pressure is an average pressure that can be applied to the distal ends of the elongated flexible members parallel to their lengths to cause the flexible members to buckle. In some embodiments, the peak pressure applied to the patient's skin during treatment can be, for example, in a range of about 4.1×10–8 (N/mm$^2$) to about 6×10$^5$ (N/mm$^2$).

In order to penetrate the skin to the desirable depth and initiate the nociceptors and then after achieving such depth, bend or buckle in order to minimize the potential damage to the skin or underlying tissue, the flexible members 325 may be designed to be at a particular distance from one another, thereby having a desired density of elongated members (filaments) per area coupled to the base place 305. Distributing and/or placing the flexible members 325 at a particular packing density allows the flexible members 325 to act independently of one another such that there is minimal interaction between adjacent flexible members to effect the bending or buckling forces between or among other flexible members. Alternatively, distributing and/or placing the flexible members 325 at a particular packing density allows the flexible members 325 to interact with one another such that the interaction between adjacent flexible members can increase the overall force or pressure required to cause the flexible members to bend or buckle. Moreover, in order to further control the bending or buckling between or among other flexible members 325, some of the flexible members may be longer or shorter than adjacent flexible members. That is, the length(s) of the flexible members 325 may vary such that a percentage or portion of the flexible members may be different than other flexible members. In some such embodiments, the shorter flexible members can provide non-penetrating contact with the skin while the longer flexible members can penetrate the skin. For example, density of flexible members per unit area may be between about 0.2 filaments per mm$^2$ and about 4.0 filaments per mm$^2$, between 0.3 filaments per mm$^2$ and about 3.9 filaments per mm$^2$, 0.4 filaments per mm$^2$ and about 3.8 filaments per mm$^2$, 0.5 filaments per mm$^2$ and about 3.7 filaments per mm$^2$, 0.5 filaments per mm$^2$ and about 3.7 filaments per mm$^2$, 0.6 filaments per mm$^2$ and about 3.6 filaments per mm$^2$, 0.7 filaments per mm$^2$ and about 3.5 filaments per mm$^2$, 0.8 filaments per mm$^2$ and about 3.4 filaments per mm$^2$, 0.9 filaments per mm$^2$ and about 3.3 filaments per mm$^2$, 1.0 filaments per mm$^2$ and about 3.2 filaments per mm$^2$, 1.1 filaments per mm$^2$ and about 3.1 filaments per mm$^2$, 1.2 filaments per mm$^2$ and about 3.0 filaments per mm$^2$, 1.3 filaments per mm$^2$ and about 2.9 filaments per mm$^2$, 1.4 filaments per mm$^2$ and about 2.8 filaments per mm$^2$, 1.5 filaments per mm$^2$ and about 2.7 filaments per mm$^2$, 1.6 filaments per mm$^2$ and about 2.6 filaments per mm$^2$, 1.7 filaments per mm$^2$ and about 2.7 filaments per mm$^2$, 1.8 filaments per mm$^2$ and about 2.6 filaments per mm$^2$, 1.9 filaments per mm$^2$ and about 2.5 filaments per mm$^2$, 2.0 filaments per mm$^2$ and about 2.4 filaments per mm$^2$, and 2.1 filaments per mm$^2$ and about 2.3 filaments per mm$^2$, and any including any value (e.g., 2.2 filaments per mm$^2$) or increment therebetween.

As mentioned above, the flexible members 325 are attached to base element 305 and extend from the distal facing side of the base element 305. The controlled stimulation device 300 also includes a driver for oscillating the base element 305 and, hence, the flexible members 325, wherein the distal ends of the flexible members 325 can move to engage with and disengage from the patient's skin. For example, the flexible member 325 can move distally and proximally of the distal face of one or more of the skin surface reference elements 340, 345. In conjunction with the design and construction of the flexible member 325, the driver of the base element 305 controls the duration of time that the flexible members engage and/or are pressed against the skin. In some embodiments, the base element 305 can include a plurality of independently-movable portions to each of which a plurality of the flexible members are coupled. Such independently-movable portion can be moved separately (physically and in time).

In some embodiments, when the flexible members 325 move in an axial direction such that the distal ends of the flexible members 325 are positioned distally of the distal face of one or more skin surface elements 340, 345, then the flexible members 325 are in a deployed (extended) position. In some embodiments, when the flexible members 325 oscillate and are in an axial position such that the distal ends of the flexible members 325 are most distal with respect to the distal face of one or more of the skin surface reference elements 340, 345, then the flexible members 325 (and base element 305 and means for oscillating) are in a fully-extended position. In some embodiments, when the flexible members 325 oscillate and are in an axial position such that the distal ends of the flexible members 325 are at a maximum proximal distance from the distal face of one or more of the skin surface reference elements 340, 345, then the flexible members 325 (and base element 305 and means for oscillating) are in a stowed (retracted) position.

Figure 3:
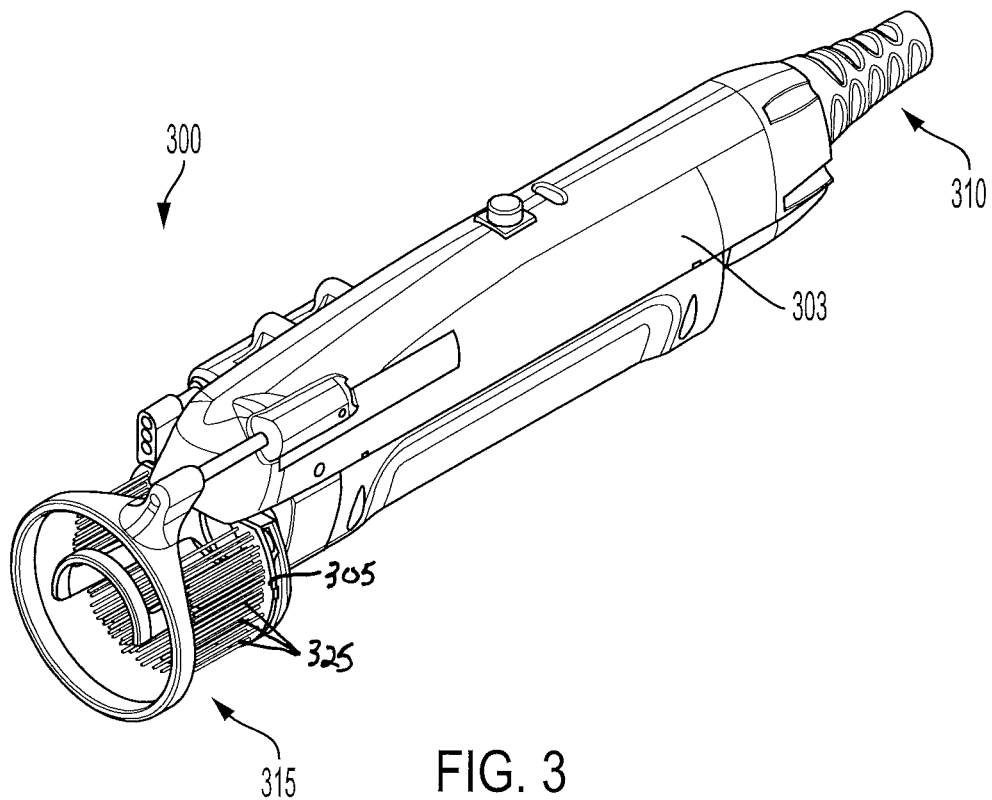
FIG. 3 is a perspective view of an example of a controlled stimulation device that may be integral with, removably coupled with, and used in conjunction with the light treatment device of FIG. 1.
Figure 4:
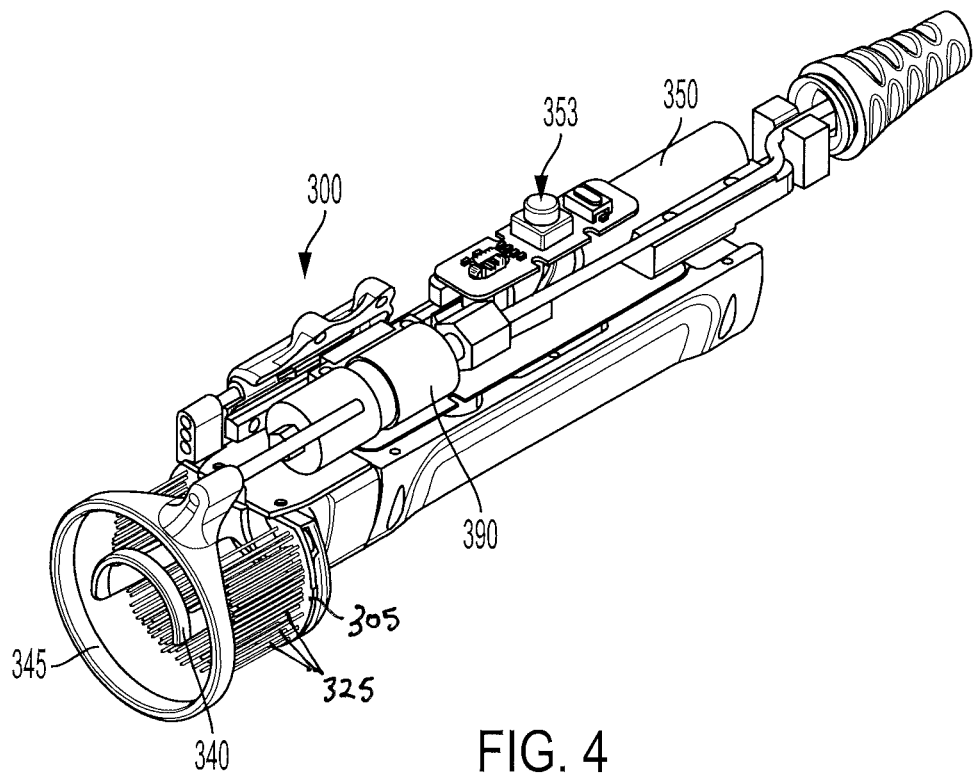
FIG. 4 is a perspective, cut-away view of the controlled stimulation device of shown in FIG. 3.
Figure 5:
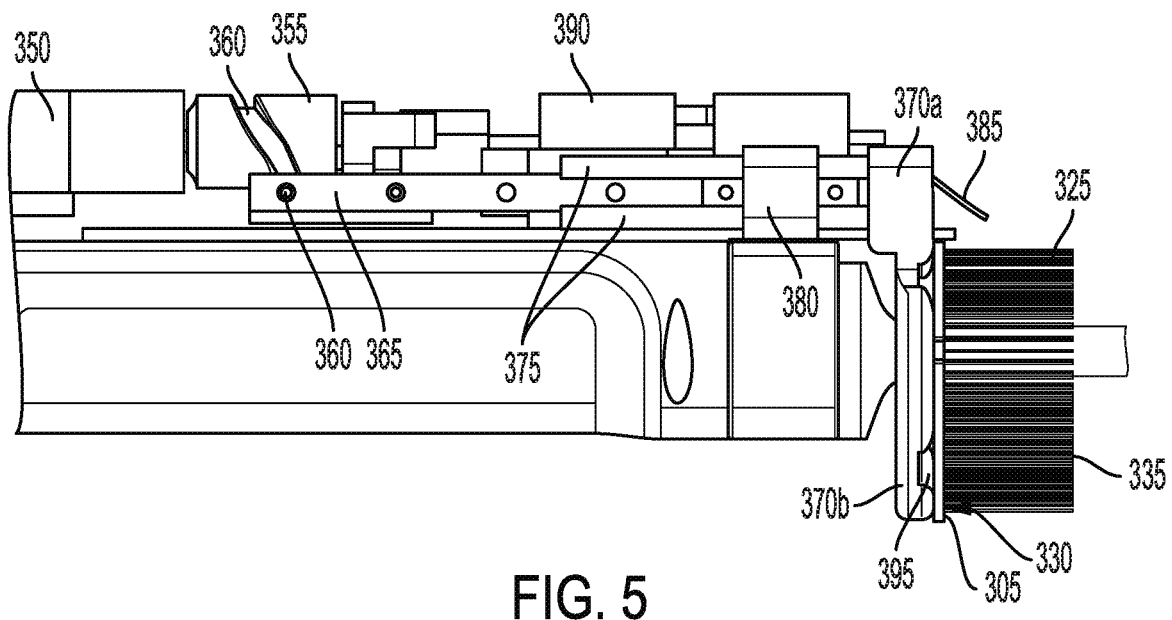
FIG. 5 is a side, cut-away view of an enlarged portion of the controlled stimulation device of shown in FIG. 3 and FIG. 4.
Figure 6:
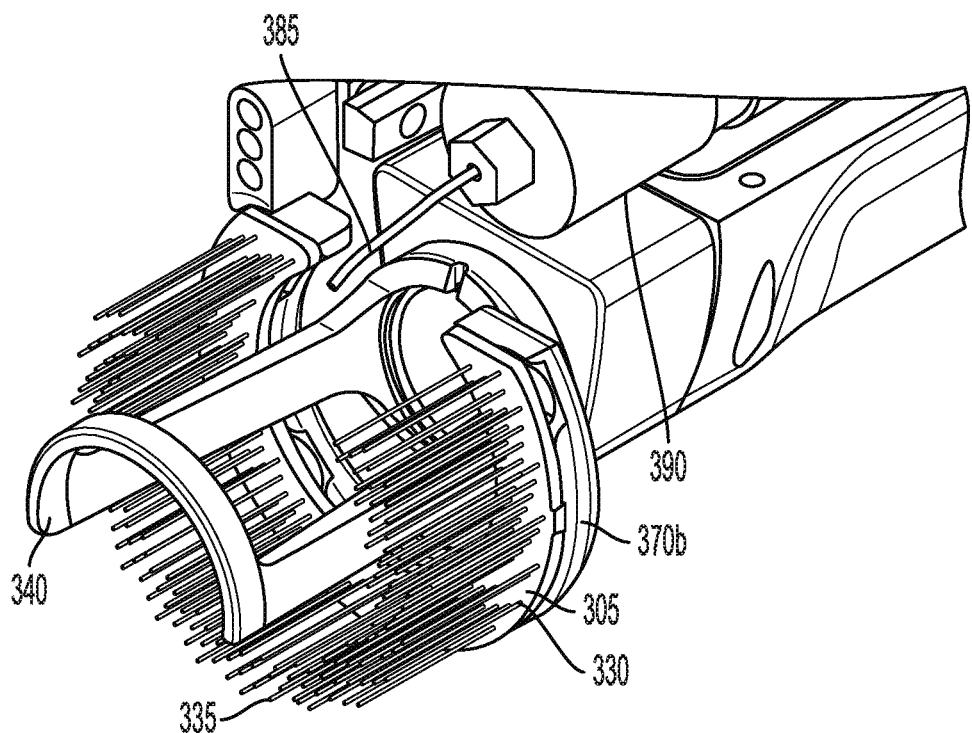
FIG. 6 is a perspective, cut-away view of an enlarged portion of the controlled stimulation device of shown in FIG. 3 and FIG. 4 from the perspective of the distal end of the controlled stimulation device.

Referring to FIG. 3, there is shown the controlled stimulation device 300 with the housing 303 encapsulating the majority of the device. Referring to FIGS. 4-6, there are shown various perspective and side, cut-away views of the controlled stimulation device 300 with a portion of the housing 303 (and other elements) removed. As shown in these figures, the controlled stimulation device 300 includes a contact plate (or ring) 340, which is disposed radially and inwardly centric of the base element 305. The contact plate 340 comprises a proximal end and a distal end, wherein the proximal end is coupled to the housing 303. In certain embodiments, it will be preferable for the contact plate 340 to contact the patient's skin regardless of whether the flexible members 325 contact the patient's skin, thus providing a skin surface reference and defining a skin surface plane. Accordingly, the distal end of the contact plate 340 may extend distally of the distal ends of the flexible members 325, particularly during movement of the base element 305 and flexible members 325 when the flexible members 325 are in a partially or extended or retracted configuration, and therefore, not contacting the patient's skin. In some embodiments, the contact plate can push against the skin such that a treatment region protrudes proximally relative to the contact plate and the flexible member can contact the treatment region while being proximal with respect to the contact plate.

Again, the controlled stimulation device 300 may also include a first contact plate (or ring) 340 disposed radially and inwardly centric of the base element 305 and flexible members 325. In some embodiments, the laser beam or laser treatment being emitted from the controlled stimulation device 300 (or other types of treatment energy, such as radiofrequency energy or mechanical energy) and/or the hand-piece 30 within or coupled to the controlled stimulation device 300 is central to the first contact plate 340. As such, the first contact plate 340 (or a portion thereof) surrounds the laser therapy path, and the flexible members 325 (or a portion thereof) surrounds the first contact plate 340. The first contact plate 340 comprises a proximal end and a distal end, wherein the proximal end is coupled to the housing 303. As discussed hereinabove, the base element 305 may have an open or closed ring-like shape, such as a square, rectangle, circular, oval, orbital, arch shaped (e.g., horseshoe shaped) plate viewed from one or both of the faces of the base element 305. Similarly, the first contact plate 340 may have an open or closed ring-like shape, such as a pole, square, rectangle, circular, oval, ellipse, orbital, arch shaped (e.g., horseshoe shaped) plate viewed from a perspective distally of the first contact plate 340. If one or both of the first contact plate 340 and the base element 305 have an opening, the orientation of the first contact plate 340 and the base element 305 may be symmetric or angularly offset, such as a configuration wherein the openings of the plates are opposite one another. The first contact plate 340 may contact the patient's skin regardless of whether the flexible members 325 contact the patient's skin. Accordingly, the distal end of the first contact plate 340 may extend distally of the distal ends of the flexible members 325, particularly during movement, e.g., oscillation, of the base element 305 and flexible members 325 when the flexible members 325 are in a partially or extended or retracted configuration, and therefore, not contacting the patient's skin. In some embodiments, the contact plate can push against the skin such that a treatment region protrudes proximally relative to the contact plate and the flexible member can contact the treatment region while being proximal with respect to the contact plate.

The controlled stimulation device 300 can also include a second contact plate (or ring) 345, which is disposed radially and outwardly concentric with the ring of flexible members 325. The second contact plate 345, therefore, surrounds the flexible members 325 (or a portion thereof), the first contact plate 340 (or a portion thereof) and the laser therapy beam, or other forms of treatment energy (such as RF). The second contact plate 345 comprises a proximal end and a distal end, wherein the proximal end is coupled to the housing 303. The second contact plate 345 may have an open or closed ring-like shape, such as a circular, oval, ellipse, orbital, arch shaped (e.g., horseshoe shaped) plate viewed from a perspective distally of the second contact plate 345. The second contact plate 345 may contact the patient's skin regardless of whether the flexible members 325 contact the patient's skin. Accordingly, the distal end of the second contact plate 345 may extend distally of the distal ends of the flexible members 325, particularly during oscillation of the base element 305 and flexible members 325 when the flexible members 325 are not contacting the patient's skin. The distal ends of the first contact plate 340 and the second contact plate 345 may be axially aligned or axially misaligned. If the first contact plate 340 and the second contact plate 345 are axially misaligned, then the distal end of the first contact plate 340 may be positioned distally of the distal end of the second contact plate 345, or vice versa.

The skin surface reference elements 340, 345 can be rigid, semi-rigid or flexible. The skin reference elements can have rounded or squared shape and assist in supporting the controlled stimulation device 300 while it is placed adjacent the skin, thereby flattening or moving the target skin surface and thereby facilitating desirable engagement of the flexible members with the patient's skin, such as the depth that the flexible members interact with the patient's skin. By way of example, in this manner, the skin reference elements can adjust the depth at which the flexible members engage the patient's skin.

The controlled stimulation device 300 may also include a driver for moving the base element 305 and, hence, the flexible members 325, wherein the distal ends of the flexible members oscillate distally and proximally toward the distal face of one or more contact plates 340, 345. The driver for moving, e.g., oscillating, the base element 305 and the flexible members 325 can include a motor 350, a cylindrical cam 355 and a linkage for coupling the cylindrical cam 355 to the base element 305. In some embodiments, the linkage can include a pin 360. The means for coupling the cylindrical cam 355 to the base element 305 can also include a rod (or drive shaft) 365 and a mount, e.g., mounting plate 370a, 370b. The rod 365 is connected to the pin 360 and the mounting plate 370a, 370b, and the base element 305 couples to the mounting plate 370b. Mounting plate 370, and mount 380 serve a chassis for the controlled stimulation device, securing the proximal end of the surface reference member 340 and providing a track along which the base element 305 can travel to move the distal ends 335 of elongated elements 325 between a stowed position and a deployed position.

The cylindrical cam 355 incudes a cam slot or groove 350, which receives the pin 360. As the motor 350 rotates, the cylindrical cam 355 also rotates and the pin 360 moves axially forward and backwards along the longitudinal axis of the counters-stimulation device 300 according to the profile of the cam slot 350. As the pin 360 moves axially forward and backwards, the base element 305 and the flexible members 325 continuously and repeatedly move from/to an (partially) extended position, a fully extended position, a partially extended position, a retracted position, and a fully retracted position. As the flexible members 325 move from a retracted position to an extended position, the flexible members 325 move toward the patient's skin and contact the patient's skin, thereby applying an increased amount of point contact, pressure and force per flexible member.

The controlled stimulation device 300 may include a motor 350 that is electrically activated via a switch 353. The motor 350 may be a direct current or alternating current motor. As such, the motor 350 may be powered by a direct current (e.g., battery) source (not shown) or a separate alternating current source. The specifications of the motor 350 and the design of the cylindrical cam 355 axially move the base element 305 and the flexible members 325 from a fully stowed (retracted) position to a fully deployed (extended) position at a rate of between about 1 Hz and about 1000 Hz, including any value or increment therebetween. The rotation of the motor 350 and the cylindrical cam 355 may be less than, equal to or greater than the rate at which the base element 305 and the flexible members 325 oscillate from a fully retracted position to a fully extended position.

The cam slot 350 of the cylindrical cam 355 also controls the amount of linear movement incurred by the base element 305 and the flexible members 325. For example, it may be desirable for the so-called stroke of the rod to be between about 0.1 mm and about 15 mm, including any value or increment therebetween, thereby causing the base element 305 and the flexible members 325 to move an axial distance of about 0.1 mm and about 15 mm in one direction (distal direction) and an axial distance of about 0.1 mm and about 15 mm in an opposite direction (proximal direction). Although the stroke of the rod may be a predetermined amount, the axial distance at which the flexible members 325 extend toward the distal face(s) of the skin surface reference elements 340, 345 may be equal to or less than such distance. For example, if the stroke of the rod is about 5 mm, it may be desirable for the flexible members 325 to extend a distance of only 3 mm beyond the distal face(s) of the skin surface reference elements 340, 345.

In certain embodiments the stroke length can be about 0.4 inches from front to back. Other stroke lengths can also work but may change the speed at which the flexible members (bristles) contact the skin. For example, a longer stroke length would require an increase in the speed that the bristles move in order to operate at the same frequency. The bristles can extend from 0.0" to 0.1" past the front plate. This can be adjustable by varying a default position of either the base plate or skin reference member. Adjustment of the depth of penetration can be advantageous in treating different parts of the body with different amounts of surface fat, i.e. less extension for a fatty sensitive area and more for a firmer less sensitive area.

Moreover, it may be desirable for the for the flexible members 325 to bend or buckle prior to extending the entire predetermined distance toward the distal face(s) of the skin surface reference elements 340, 345. Continuing with the previous example, therefore, it may be desirable for the flexible members 325 to extend a distance equal to 0.5 mm before the distal face, a distance equal to the distal face(s) or a distance of 1 mm beyond the distal face(s) of the skin surface reference elements 340, 345 to come into contact with or penetrate into the skin of the patient, and if so, the flexible members 325 will be designed to bend or buckle prior after traveling 1 mm of the 3 mm distance toward the distance beyond the distal face(s) of the skin surface reference elements 340, 345. As such, the flexible member 325 will bend and/or buckle about 2 mm after the flexible member contacts and/or penetrates the patient's skin to the desirable depth.

Furthermore, as mentioned above, it may desirable for the flexible members 325 to engage and/or press against the skin for certain period of time. Such time may be controlled by the configuration of the cam slot 350 of the cylindrical cam 355. For example, the cam slot 350 may include a percentage of its length to correlate to the time during which the flexible members 325 are in a relatively static axial position during rotation of the cylindrical cam 355. The relatively static position may include a partially extended position, a fully extended position, a partially retracted position, and/or a fully retracted position.

Moreover, it may be desirable for the flexible members 325 to continuously engage with and/or press against the skin with a variable pressure and/or force such that the flexible members 325 maintain engagement with the skin when the base element 305 and flexible members are in a partially extended position, a fully extended position, a partially retracted position, and a fully retracted position. That is, the nociceptors may be activated, and the amount of pain perceived by the patient may be reduced, even if the flexible members do not retract to a position away from the skin but as long as the amount of pressure, force or engagement of the flexible members 325 varies. As such, the positions of the dimensions of the flexible members 325, skin surface reference elements 340, 345, and cam slot 350 can be designed such that the flexible members 325 extend toward the distal end of the skin surface reference elements 340, 345 when the flexible members 325 and base element 305 are in a partially extended position, a partially retracted position, and/or a fully retracted position in addition to a fully extended position. As such, the flexible members 325 can continuously engage and/or press against the skin with varying pressure.

The controlled stimulation device 300 may include means for axially adjusting the position(s) of the base element 305 and the flexible members 325. Such adjustment means may include a mount 380, which is fixedly coupled to the rod 365, and one or more supports 375, which are fixedly coupled to the mounting plate 370a. The supports 375 can be slidably coupled to the mount 380, such that the supports 375 can slide with respect to the mount 380, thereby providing an operator the ability to collectively and slidably adjust the mounting plate 370a, the base element 305 and the flexible members 325 with respect to the housing 303.

In some embodiments of the controlled stimulation device 300, the base element 305 and the flexible members 325 can be removably coupled to/from the remainder of the controlled stimulation device 300. Because the flexible members 325 engage with and in some cases pierce the patient's skin, it may be desirable to dispose of the base element 305 and/or the flexible members 325 after use on a given patient. But for economic reasons, it may be desirable to re-use the remainder of the controlled stimulation device 300. Accordingly, the controlled stimulation device 300 may include releasable clamp or fitting for removably coupling the base element 305 and/or the flexible members 325 to the controlled stimulation device 300. By way of example and referring to FIG. 5, there is shown one such means, which includes a magnet 395 that is attached to or integral with the base element 305. Regardless of whether the base element 305 is constructed of metal or plastic, if the base element 305 includes the magnet 395, it will be desirable for the mounting plate 370b to be constructed of metal or have a mating magnet (not shown). Although not shown, an alternative means for removably coupling the base element 305 and/or the flexible members 325 from the controlled stimulation device 300 may include a twist mechanism, a press-fit mechanism, and/or a snap-fit mechanism such that the base element 305 and mounting plate 370b can matingly engage and disengage.

In some embodiments, the controlled stimulation device 300 can be in the formed of a cartridge that can be removably coupled to a treatment device. In some embodiments, the cartridge, in addition to the base element 305, the flexible members 325 and one or more reference elements 340, 345, can also include a motor and the requisite linkage, such as those discussed above, for moving the base plate and the flexible members. In some embodiments, the motor and the linkage can be disposed in a sleeve that can be coupled to an outer surface of the treatment device, e.g., the outer surface of a handpiece associated with the treatment device. In other embodiments, the motor and the linkage can be disposed in the treatment device, and upon coupling of the cartridge with the treatment device, the cartridge can be coupled to the linkage.

The controlled stimulation device 300 may include multiple sets of flexible members 325 such that each set or multiple sets of flexible members 325 have different characteristics. Specifically, one or more sets of flexible members 325 may have a first material, size (e.g., length, diameter, circumference), cross-sectional area, and tip shape; and one or more sets of flexible members 325 may have a second material, length, cross-sectional area, and tip shape. The number of differing characteristics between each set of flexible members 325 may be one or more, including a plurality of some or all characteristics. For example, one set of flexible members 325 may have a first length such that the first set of flexible members 325 extend from the base element 305 a first distance, as well as oriented at an angle and a particular distance with respect to the skin surface reference elements 340 and/or 345, and another set of flexible members 325 may have a second length such that the second set of flexible members 325 extend from the base element 305 a second distance, as well as being oriented at a different angle and/or distance relative to the skin surface reference elements 340 and/or 345. In some such embodiments, the flexible members 325 have the same material, diameter, circumference, cross-sectional area, and tip shape. More specifically, the length of the first set of flexible members 425 may extend a first distance during oscillation (proximally of, at, or distally of the skin surface reference elements 340 and/or 345), and the second set of flexible members 425 may extend a second distance during oscillation (proximally of, at, or distally of the skin surface reference elements 340 and/or 345). An alternative example may include both sets of flexible members 325 having the same lengths, but one set of flexible members 325 may have a first material, diameter, circumference, cross-sectional area, and tip shape, and the second set of flexible members 325 may have a second material, diameter, circumference, cross-sectional area, and tip shape, such as one set having a flat distal end and the other set having a distal end with at least one of the following shapes: a round point, a star point, a cross point, a tapered face, a beveled face, a multi-facet face, and/or a conical, spherical, elliptical, or hyper-elliptical shape, without or without grooves, e.g., micro-ridges or micro-lines. A further example may include both sets of flexible members 325 having different lengths and one or more different materials, diameters, circumferences, cross-sectional areas, and tip shapes, wherein different lengths, materials, diameters, circumferences, cross-sectional areas, and tip shapes, affects the flexibility, bend resistance, sharpness, and/or rigidity of the flexible members 325 ability to penetrate the skin a certain depth. The different lengths and one or more different materials, diameters, circumferences, cross-sectional areas, and tip shapes of the flexible members may limit the skin's exposure to one set of flexible members because one set (i.e., shorter) of flexible members may have decreased bending properties relative of the other (i.e., longer set) of flexible members, thereby allowing the first set to act in a mechanical fashion similar to a skin surface reference element relative to the other set of flexible members.

Figure 7:
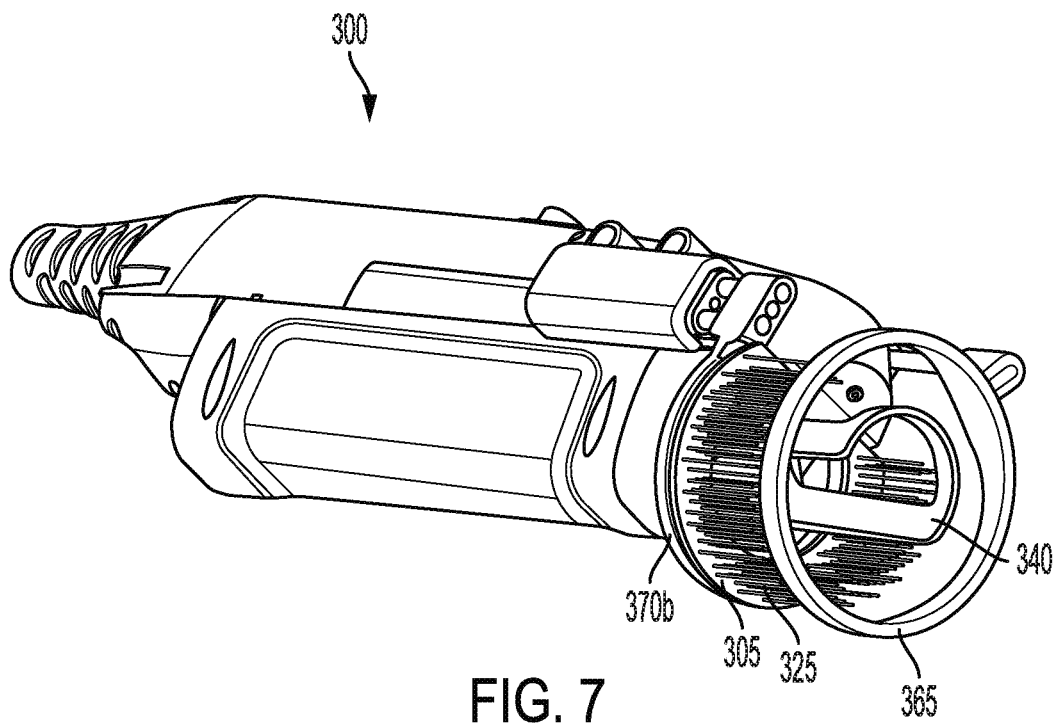
FIG. 7 is an alternative perspective view of the controlled stimulation device of FIG. 3 from one side of the controlled stimulation device.
Figure 8:
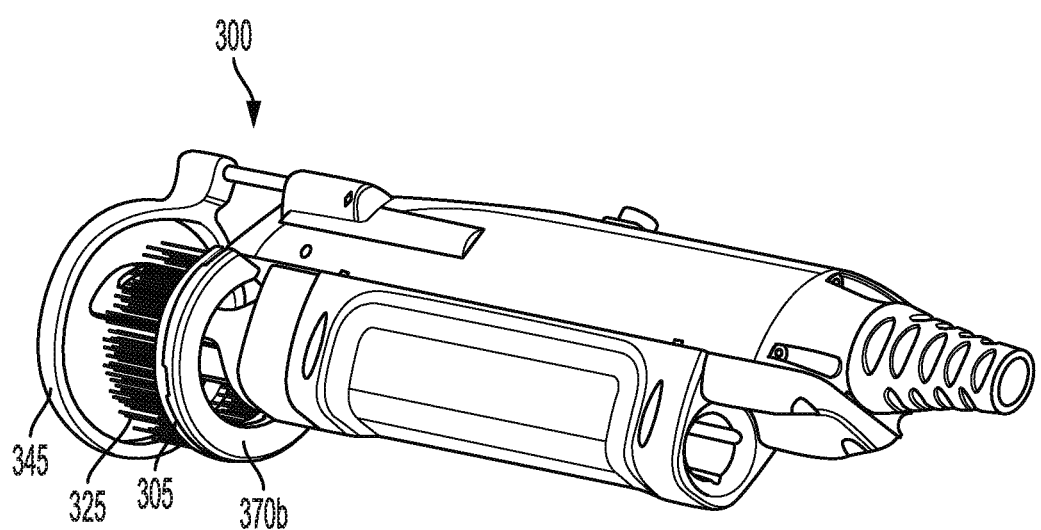
FIG. 8 is another alternative perspective view of the controlled stimulation device of FIG. 3 from the other side of the controlled stimulation device.
Figure 9:
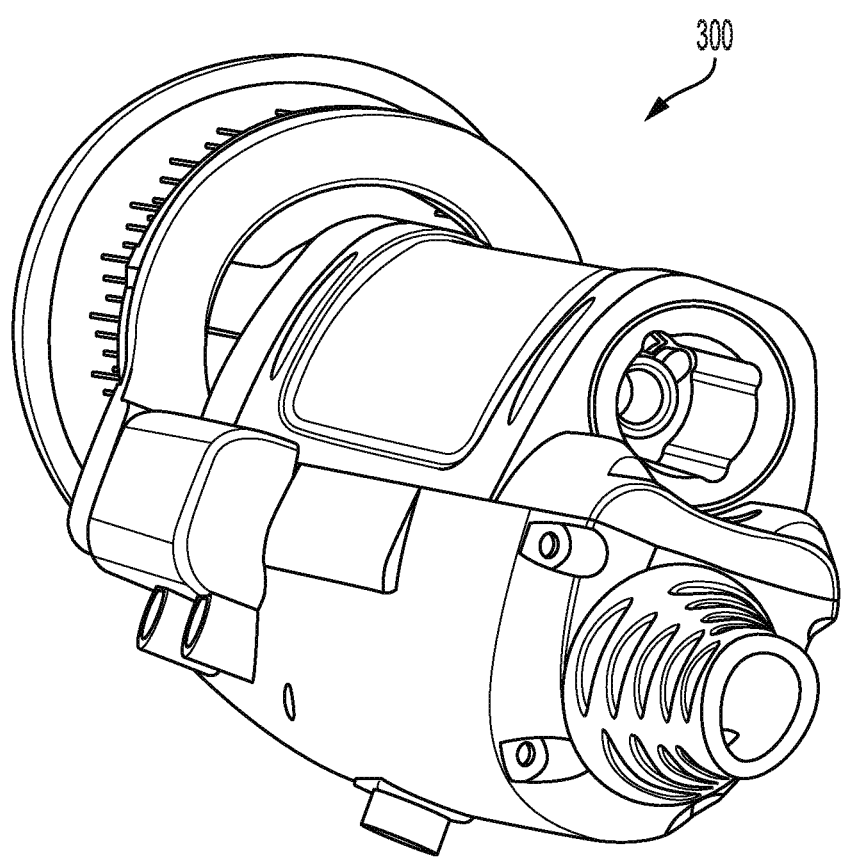
FIG. 9 is an enlarged perspective view of the controlled stimulation device of FIG. 3 from the perspective of the proximal end of the controlled stimulation device.
Figure 10:
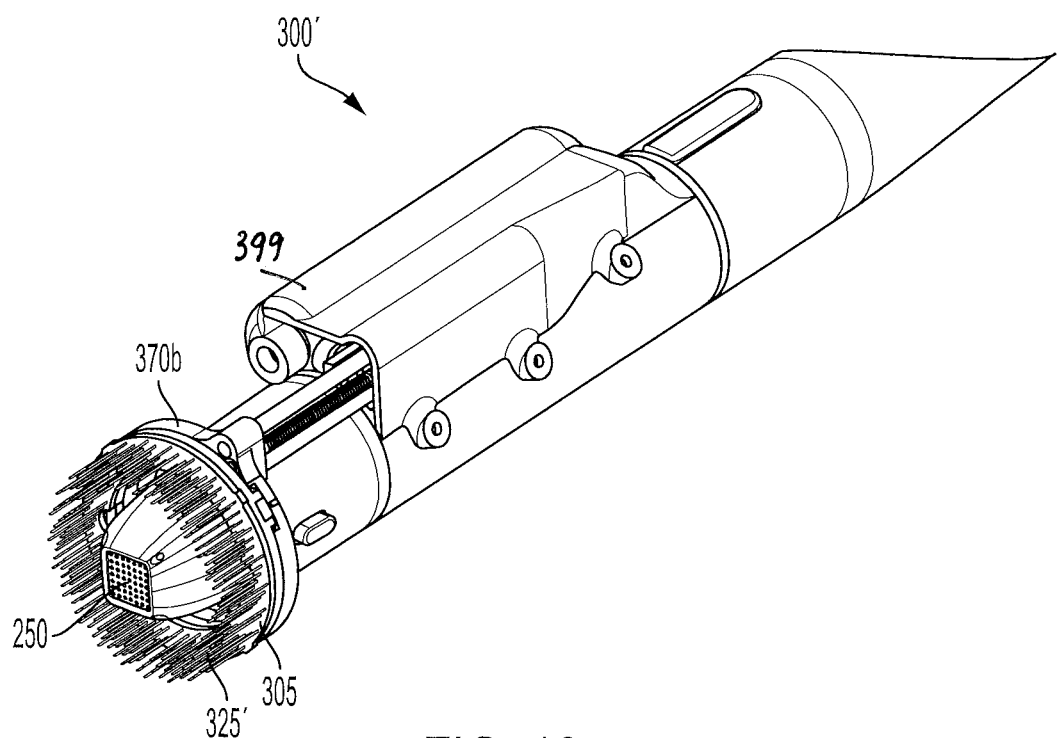
FIG. 10 is a perspective view of another example of a controlled stimulation device that may be integral with, removably coupled with, and used in conjunction with the RF microneedle device of FIG. 2.
Figure 11:
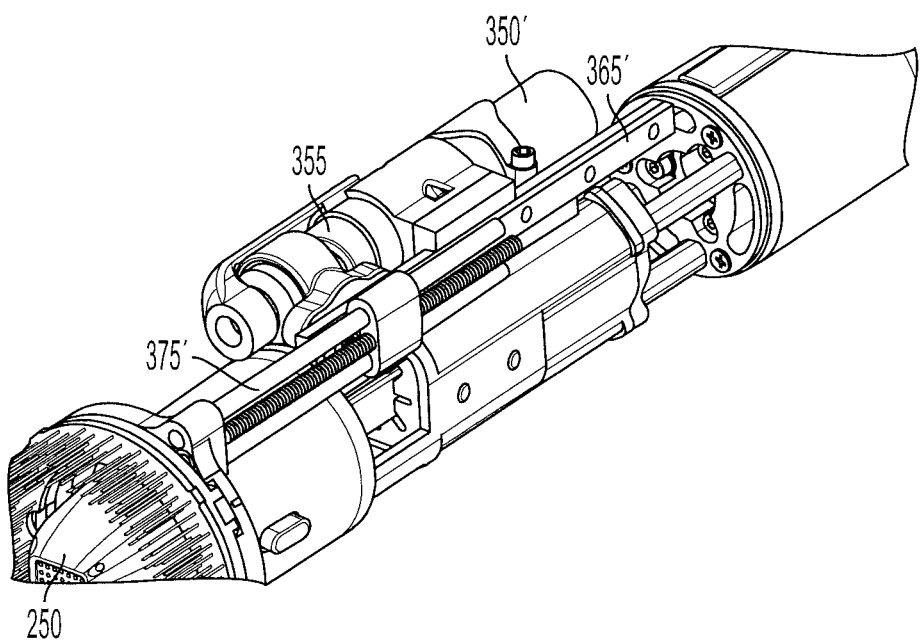
FIG. 11 is a perspective, cut-away view of the controlled stimulation device of shown in FIG. 10.
Figure 12:
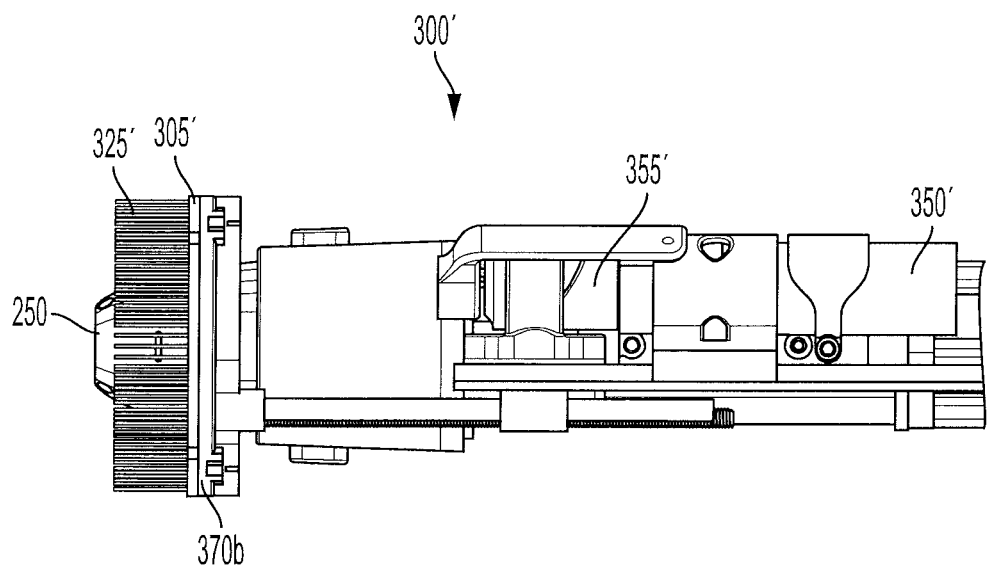
FIG. 12 is a side, cut-away view of an enlarged portion of the controlled stimulation device of shown in FIG. 10 and FIG. 11 from one side of the controlled stimulation device.
Figure 13:
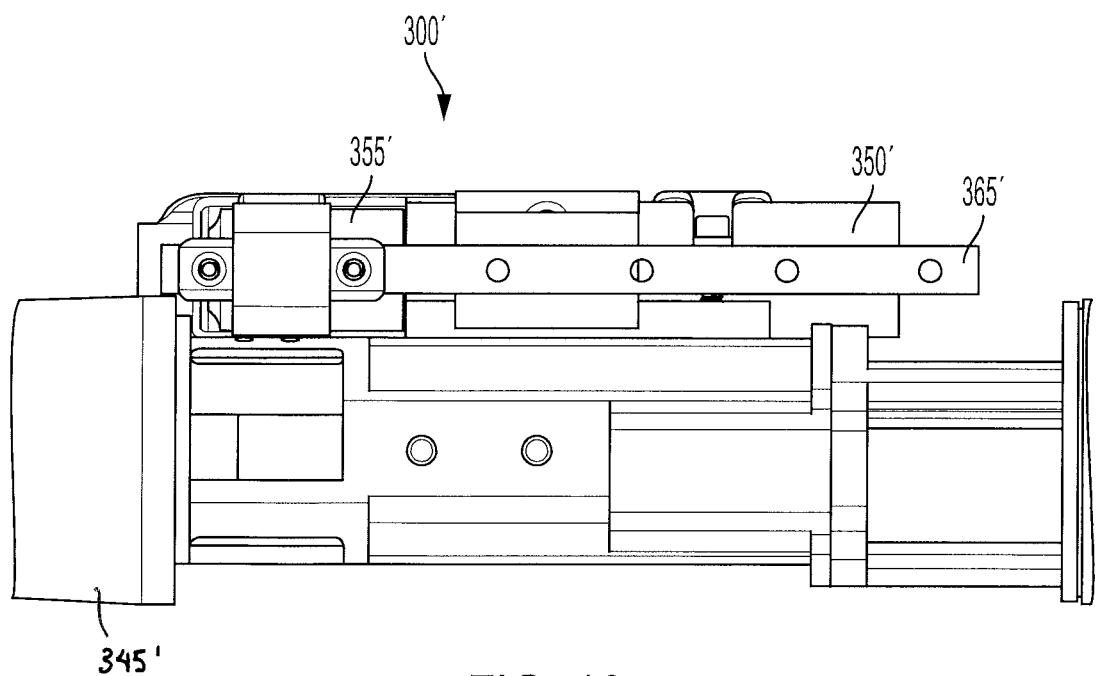
FIG. 13 is a side, cut-away view of an enlarged portion of the controlled stimulation device of shown in FIG. 10 and FIG. 11 from the other side of the controlled stimulation device.

Referring to FIGS. 5 and 6, the controlled stimulation device 300 may include means for cooling the patient's skin during application of the light-based treatment (e.g., laser) treatment. For example, the means for cooling may include a fluid reservoir 390 and a nozzle 385 for dispensing the fluid (such as cryogen) onto the skin prior to, during and/or after application of the laser energy or electromagnetic radiation. FIG. 7 is an alternative perspective view of the controlled stimulation device of FIG. 3 from one side of the controlled stimulation device. FIG. 8 is another alternative perspective view of the controlled stimulation device of FIG. 3 from the other side of the controlled stimulation device. FIG. 9 is an enlarged perspective view of the controlled stimulation device of FIG. 3 from the perspective of the proximal end of the controlled stimulation device;

Referring to FIGS. 10-13, there is shown another example of a controlled stimulation device 300' that may be integral with, removably coupled with, and used in conjunction with the RF microneedle device 100 of FIG. 2. For example, the hand piece 250 of the RF microneedle device 100 can be used in conjunction with the controlled stimulation device 300'. The controlled stimulation device 300' shown in FIGS. 10-13 is similar to the controlled stimulation device 300 shown in FIGS. 3-9 except the controlled stimulation device 300' shown in FIGS. 10-13 is used in conjunction with a hand piece 250 from an RF microneedle treatment device 100 rather than a laser treatment hand piece. As such, similar reference numbers are used in FIGS. 10-13 but with the addition of a prime symbol ('). In the embodiment of FIG. 10-13, the chassis can further include a sheath 399 for housing the motor and mount that provide longitudinal movement of the base plate and/or the elongate flexible members. The sheath 399 essentially allows the drive elements or the flexible members to "piggy-back" on a conventional RF micro-needle treatment device. In this embodiment, the skin-contacting face of RF electrode array 250 can also serve as a skin reference element.

Although it is not shown, either the controlled stimulation device 300, 300' may further include a controller configured to obtain feedback during treatment and/or include input and/or output ports and/or components. Generally, the controller may include one or more processors, memory and one or more modules that contain logic or instructions stored in memory for controlling the operation of the controlled stimulation device and the laser treatment device or the RF microneedle treatment device. For example, the controller may include logic that coordinates the application of the treatment (e.g., laser light or RF microneedles) and the movement of the flexible members of the controlled stimulation. As such the timing of the flexible members contacting the patient's skin may, therefore, be synchronized with the treatment device, such that flexible members contacting the patient's skin may be coordinated with the timing of the treatment device onset (e.g., 1 to 200 msec prior to treatment activation), during activation of the treatment device or after activation the treatment device. The controller may include logic that allows the user of the controlled stimulation device to adjust the timing (phase of oscillation motion or pulsed engagement) in order to optimize the benefits of the pain reduction for each patient.

Figure 14:
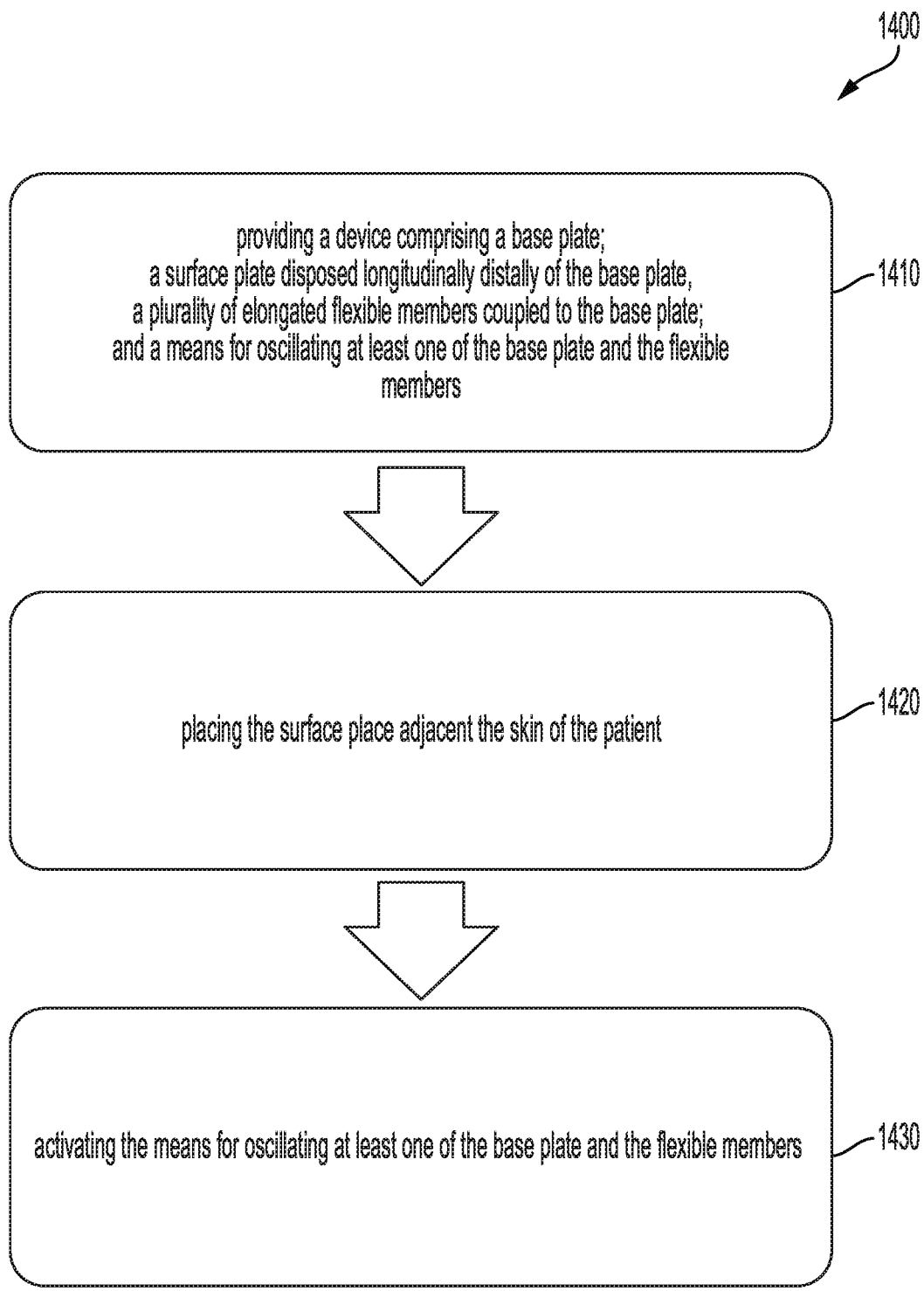
FIG. 14 is a block diagram or flow chart of operating and/or using the controlled stimulation device(s) discussed herein.
Figure 16A:
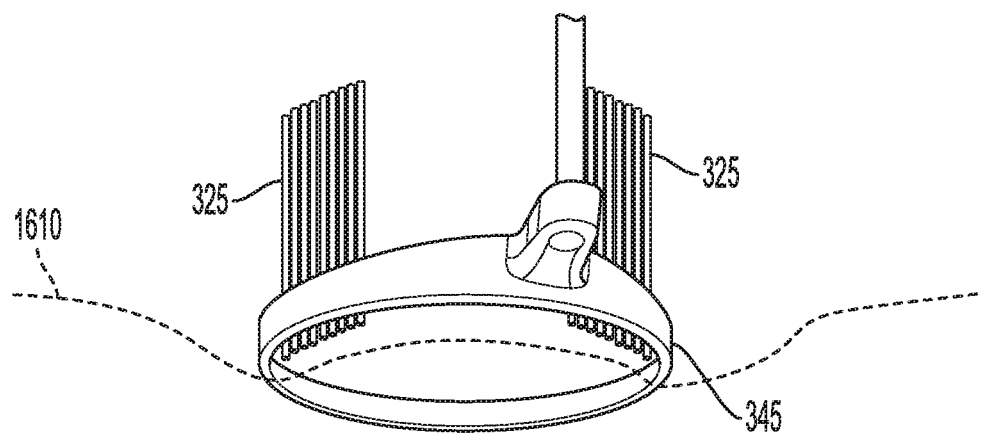
FIGS. 16A, 16B and 16C are illustrations of different variations of the controlled stimulation device adjacent the skin of a patient.
Figure 16B:
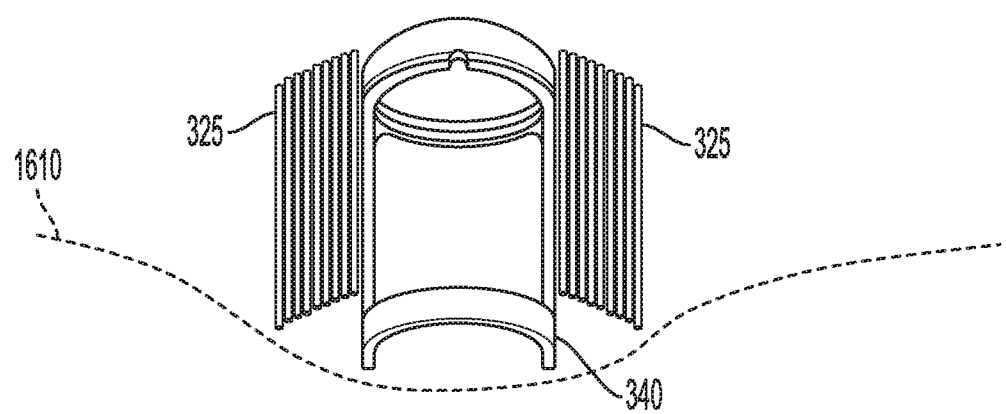
Figure 16C:
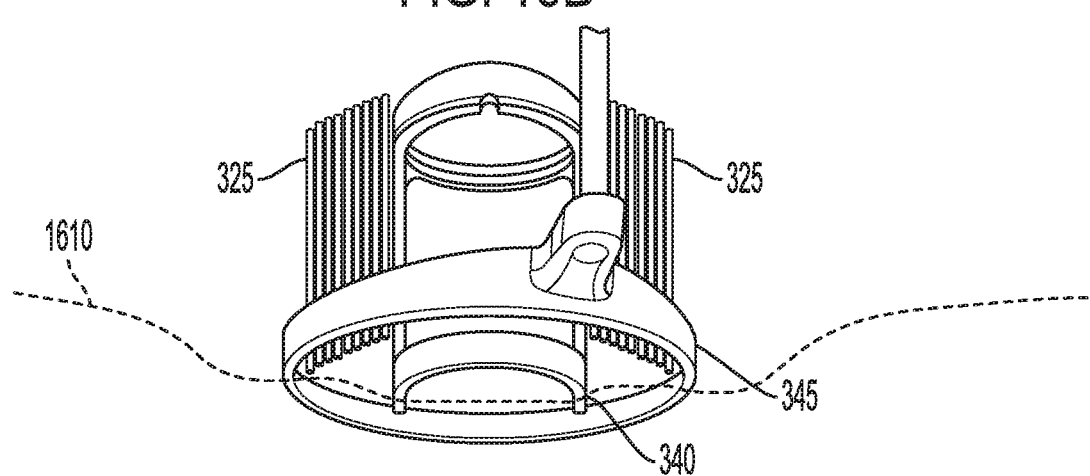

Referring to FIG. 14, there is shown a block diagram or flow chart of a method of operating and/or using the controlled stimulation device(s) to reduce the potential pain a patient experiences prior to, during, and/or after treatment. The method of applying controlled stimulation to a patient 1400 may include the steps of providing a controlled stimulation device 1410 adjacent the skin of the patient. For example, the controlled stimulation device may comprises a base element, a skin surface reference element (surface plate in FIG. 14) disposed longitudinally distally of the base element (base plate in FIG. 14), the skin surface reference element comprising a distal face a plurality of elongated flexible members coupled to the base element, each of the plurality of flexible members comprising a proximal end and a distal end, and means for oscillating the base element and the flexible members, wherein the distal ends of the flexible members oscillate distally and proximally with respect to the distal face of the skin surface reference element. Assuming the controlled stimulation device includes a skin surface reference element, the method 1400 comprises the step of locating/applying the skin surface reference element 340 and/or 345 adjacent the skin 1610 of the patient as illustrated in either FIG. 16A or FIG. 16B, and activating the means for oscillating at least one of the base element and the flexible members 325. Upon activation of the oscillating means, the flexible members 325 can oscillate between a deployed position (FIGS. 16A and 16C) and a stowed position (FIG. 16B) to repeatedly engage and disengage the skin of the patient, thereby activating the nociceptors. As shown in FIG. 16C, it may also be desirable to include two skin surface reference elements 340, 345 with the flexible members 325 disposed radially therebetween, thereby further increasing the interaction between the flexible members 325 and the patient's skin 1610. For example, when the two plates 340, 345 contact with the skin, the pressure of plates 340, 345 against the skin may cause the skin 1610 to protrude proximally of the surface of the plates. Such bulging of the skin, may allow the point of contact between the flexible members 325 and the skin 1610 to be above the plane of the reference plates or the distal portions of the reference plates.

It may be desirable for the flexible members to oscillate in a direction normal to the skin of the patient. If so, it may also be desirable for the method to include the step of moving the device along the skin of the patient while maintaining placement of the skin surface reference element adjacent the skin of the patient and simultaneously oscillating the flexible members to engage and disengage the skin of the patient. The disengagement of the flexible members from the skin minimizes potential irritation and/or damage to the skin or underlying tissue caused by the interaction of the flexible members and the skin, particularly if the flexible members are moved horizontally across the skin surface while continuously engaged with the surface.

Figure 15:
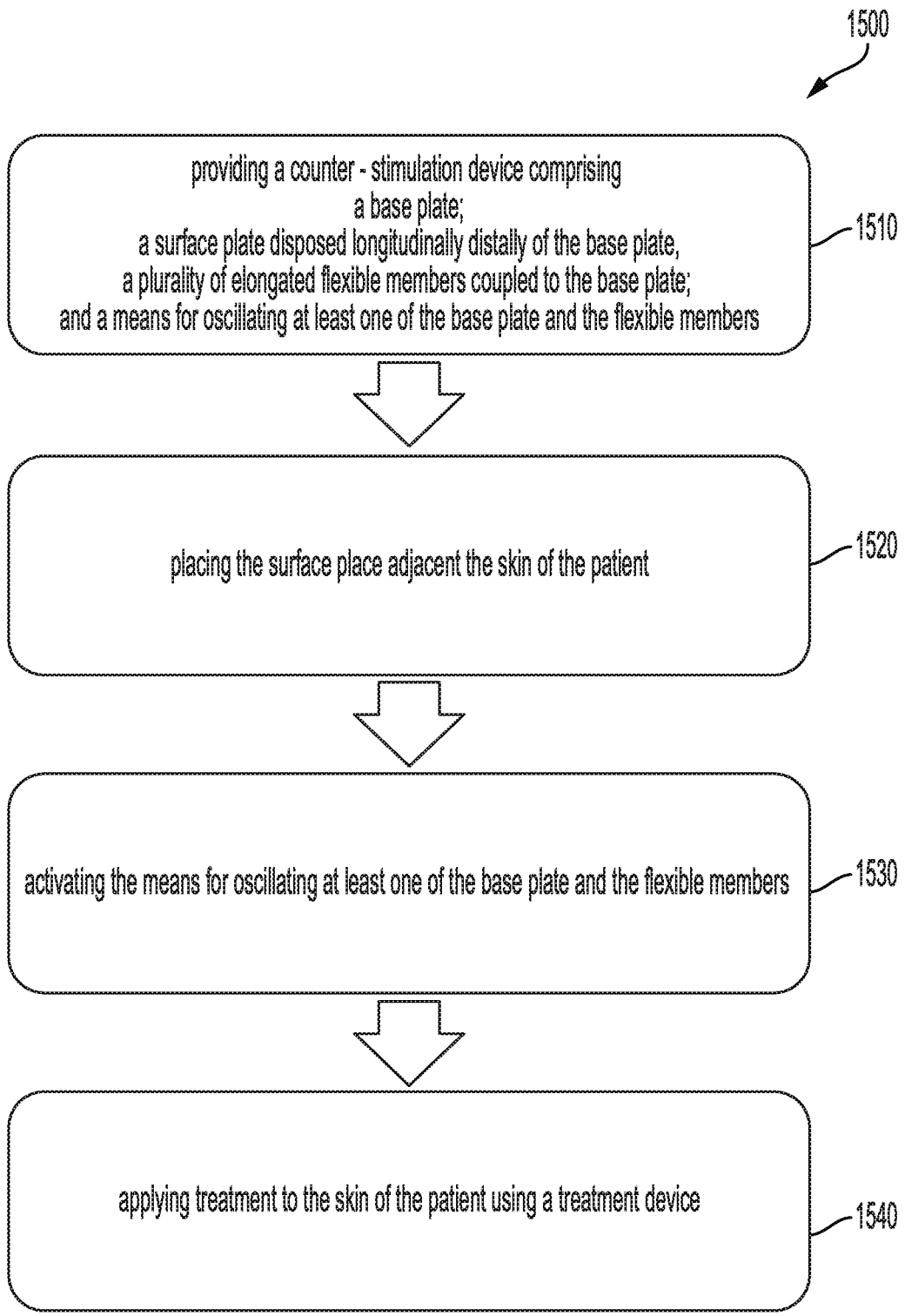
FIG. 15 is a block diagram or flow chart of a method of treatment using the controlled stimulation device(s) and the treatment device(s) discussed herein.

Referring to FIG. 15, there is shown a block diagram or flow chart of a method of operating and/or using the controlled stimulation device(s) described herein to reduce the potential discomfort and pain a patient may experience prior to, during, and/or after treatment using a treatment device described herein. The method of applying controlled stimulation to a patient 1500 may include the steps of positioning a controlled stimulation device 1510 adjacent the skin of the patient. As discussed above, the controlled stimulation device may comprise a base element, a skin surface reference element disposed longitudinally distally of the base element, the skin surface reference element comprising a distal face, a plurality of elongated flexible members coupled to the base element, each of the plurality of flexible members comprising a proximal end and a distal end, and means for oscillating the base element and the flexible members, wherein the distal ends of the flexible members oscillate, for example, distally and proximally with respect to the distal face of the skin surface reference element. It may also be desirable for the method 1500 to include the step of locating the skin surface reference element adjacent the skin of the patient 1520, and activating the means for oscillating the base element and the flexible members 1530. Upon activation of the oscillating means, the flexible members can oscillate, e.g., continuously, to repeatedly engage with and disengage from the skin of the patient, thereby activating the nociceptors. The nociceptors may be activated before, during and/or after treatment. Upon activating the nociceptors, treatment is applied to the skin of the patient 1540 using a treatment device, such as those described herein. For example, the treatment device may comprise an array of microneedles, an array of microneedles that are capable of emitting radiofrequency energy or one or more laser emitters capable of emitting laser energy. Alternatively, or in addition, the treatment device can include a mechanical element, such as an array of needles, for application of treatment to the skin.

In order to enable effective discomfort and pain reduction, the flexible members can be arranged within the controlled stimulation device such that they radially surround at least a portion of treatment region. Additionally, the skin surface reference element may be radially disposed relative to the flexible members. For example, one or more skin surface reference elements may be disposed radially inward and/or outward of the flexible members to provide a support surface against which the skin is pressed. As discussed above, the flexible members 325 are attached to the base element 305, and the flexible members move with the base element. The skin surface reference elements 340, 345 may also be adjustable and move relative to the base element 305 and the flexible members 325. The distance between the distal end of the flexible members and the skin surface reference element may be adjustable.

In a further effort to improve effectiveness of discomfort and pain reduction, the controlled stimulation device can also include mechanisms for moving the base element and the flexible members in a lateral direction or a rotational direction normal to the direction of the longitudinal axis of the flexible members and normal to the surface of the skin or tissue being treated, thereby varying the position on the skin or tissue where the elongated flexible members impact the skin or tissue during oscillation of the flexible members, for example, in a direction distally and proximally of the distal face of the skin surface reference element and potentially enhancing the ability of the device to stimulate or elicit the desired effect on the skin or tissue. The means for moving the base element and the flexible members in a lateral direction or a rotational direction normal to the direction of the longitudinal axis of the flexible members and normal to the surface of the skin or tissue being treated may include an additional motor, cam, etc. or the means for moving the base element and the flexible members in a lateral direction or a rotational direction normal to the direction of the of the longitudinal axis of the flexible members and normal to the surface of the skin or tissue being treated could be coupled to and combined with the means for oscillating at least one of the base element 305 and the flexible members 325 such that only one motor 350 is required. Moving at least one of the base element and the flexible members in a lateral direction or a rotational direction normal to the direction of the of the longitudinal axis of the flexible members and normal to the surface of the skin or tissue being treated can minimize and/or reduce and/or prevent the distal ends of elements repeatedly contacting the tissue in the exact, same or similar location multiple times, so as to prevent habituation or otherwise more effectively condition the tissue or its sensory aspects of skin or tissue while the flexible members move perpendicularly (in an up and down motion) relative to the skin and/or tissue that the elongated flexible members contact. The lateral or rotational direction may also vary such that the lateral or rotational movement of the flexible members is non-uniform, thereby potentially further enhancing the device's effect, particularly when the device is located for a period of time on a particular area of the skin or tissue in a repetitive and/or stamping fashion and not subject to continuous movement across the surface of the tissue or skin.

Referring to FIG. 17-20, there is shown another example of a controlled stimulation device 1700 that may be removably coupled with and used in conjunction with a light emitting portion 2 of a light treatment device, which may be the same as or similar to the light treatment device 1 of FIG. 1. The light emitting portion 2 is received in an internal passageway (not shown) of the controlled stimulation device 1700 and emits light at the distal end 1735 of the controlled stimulation device 1700. As such, the distal end 1735 of the controlled stimulation device 1700 is considered the treatment end of the device.

Figure 17:
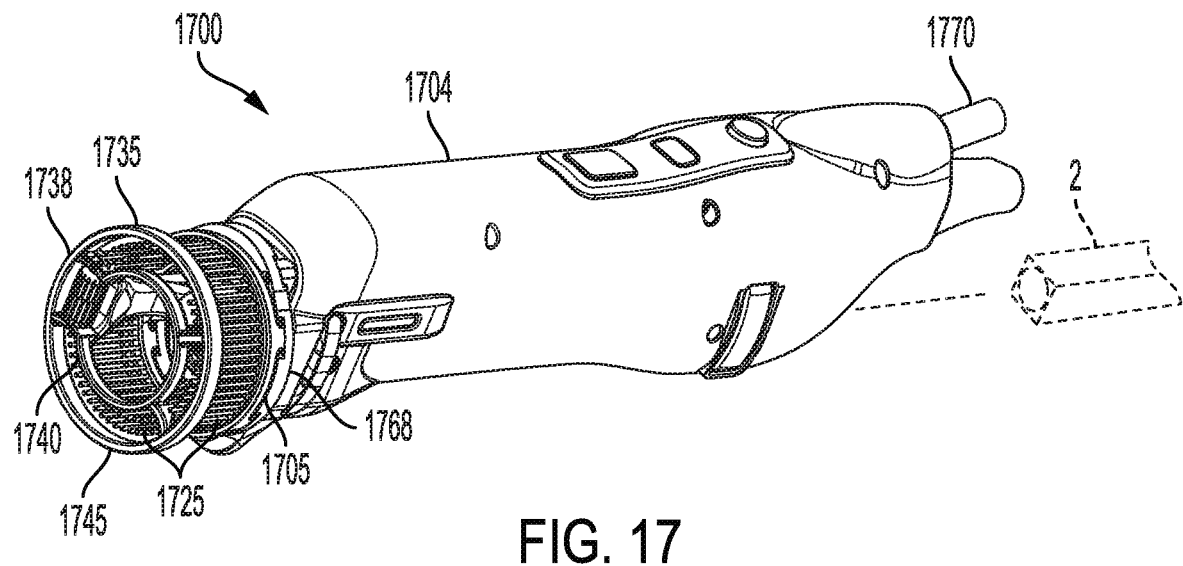
FIG. 17 is a perspective view of another example of a controlled stimulation device that may be removably coupled with a light treatment device.
Figure 18:
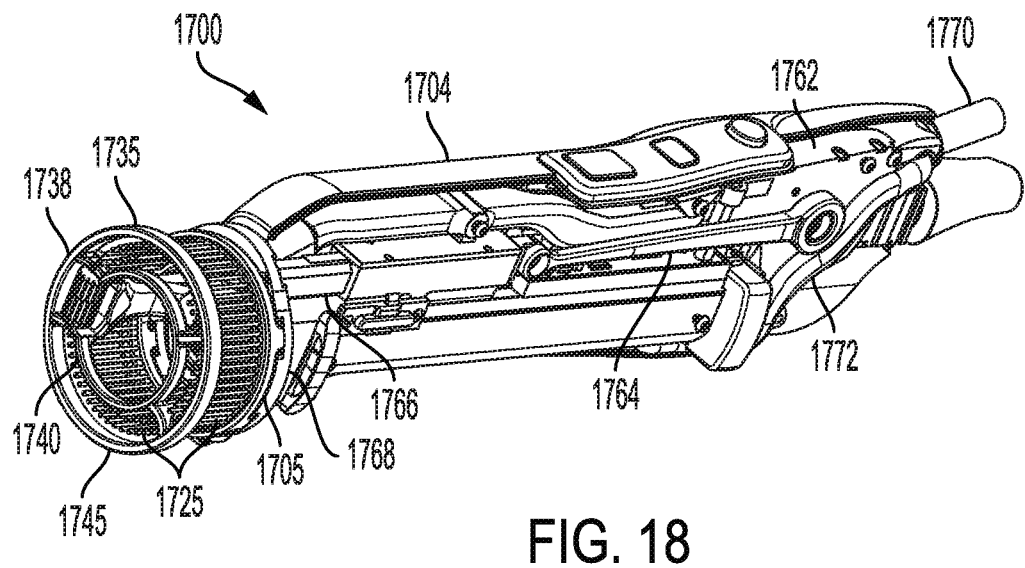
FIG. 18 is another perspective view of the controlled stimulation device of FIG. 17 with a portion of a housing of the controlled stimulation device being removed to illustrate internal features of the device.
Figure 19:
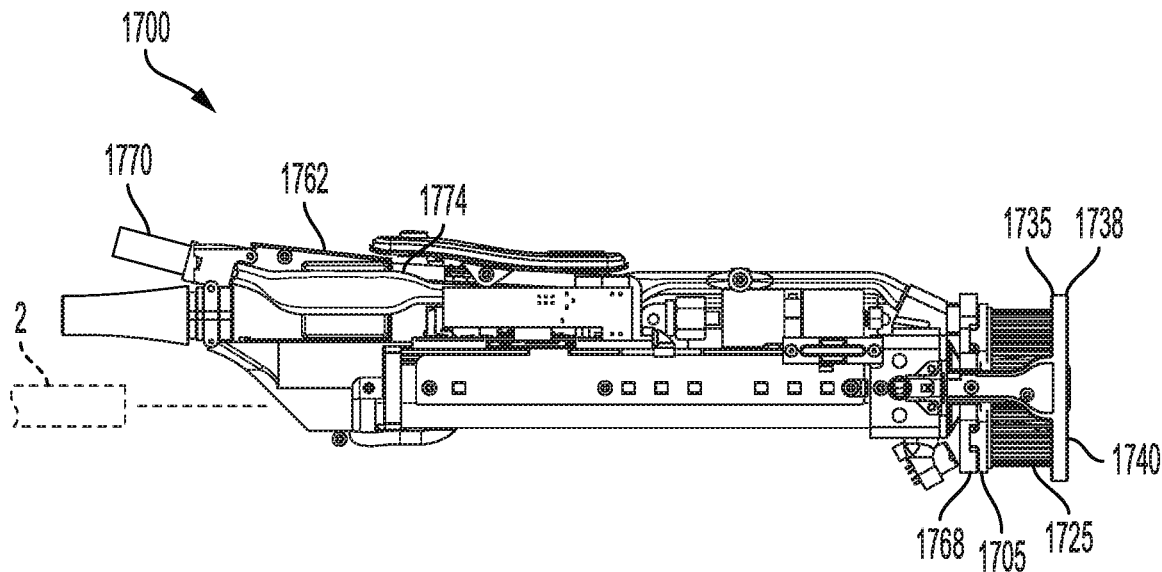
FIG. 19 is a side view of the controlled stimulation device of FIG. 17 with the housing being removed to illustrate internal features of the device.
Figure 20:
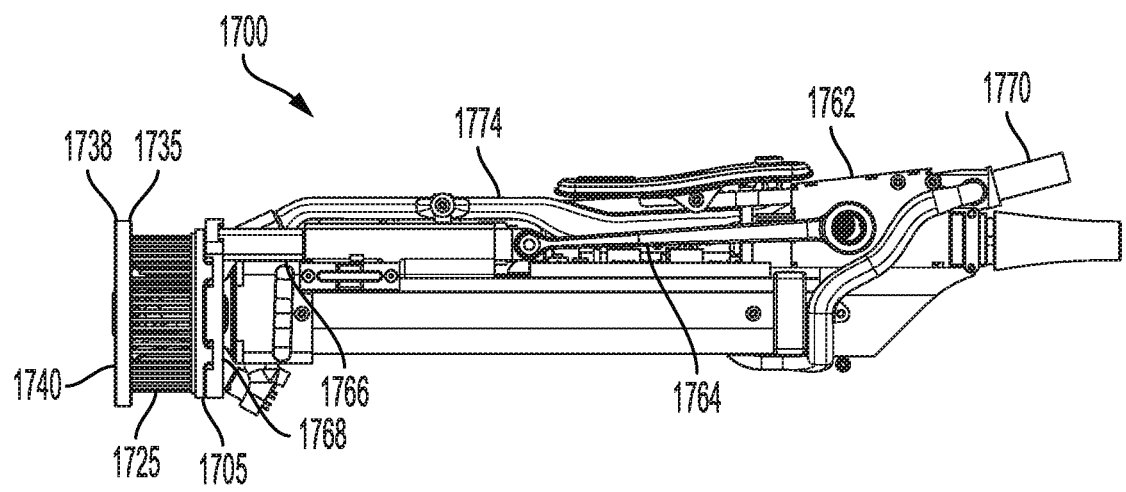
FIG. 20 is an opposite side view of the controlled stimulation device of FIG. 17 with the housing being removed to illustrate internal features of the device.

Referring to FIG. 17, there is shown the controlled stimulation device 1700 with a housing 1704 encapsulating the majority of the device. Referring to FIGS. 18-20, there are shown various views of the controlled stimulation device 1700 with portions of the housing 1704 removed to illustrate internal features. In a similar manner to the devices described above, the treatment end of the controlled stimulation device 1700 includes a base element 1705 (or base ring) that carries a plurality of flexible members 1725 and a surface reference assembly 1738 (or surface ring assembly or contact plate assembly) disposed distally of the base element 1705. Generally, the skin surface reference element assembly 1738 includes an inner skin surface reference element 1740 and an outer skin surface reference element 1745 between which the flexible members 1725 are radially disposed. Further details of the base element 1705, the flexible members 1725, and the skin surface reference elements 1740, 1745 are provided below.

The controlled stimulation device 1700 includes a means for oscillating the base element 1705 and the flexible members 1725 relative to the skin surface reference elements 1740, 1745, and distal ends of the flexible members 1725 oscillate, for example, distally and proximally of distal faces of the skin surface reference elements 1740, 1745 (for example and as described above, between deployed position and a stowed orretracted position, and/or by a predetermined distance, such as between 0.25 mm and 7.5 mm, more specifically from about 0.5 mm to 5 mm). In certain embodiments the stroke length can be about 0.4 inches from front to back. Other stroke lengths can also work but may change the speed at which the bristles contact the skin. For example, a longer stroke length would require an increase in the speed that the bristles move in order to operate at the same frequency. In some embodiments, the bristles can extend from 0.0" to 0.1" past the front plate. This can be adjustable by varying a default position of either the base plate or skin reference member. Adjustment of the depth of penetration can be advantageous in treating different parts of the body with different amounts of surface fat, i.e. less extension for a fatty sensitive area and more for a firmer less sensitive area.

As illustrated, the linkage for oscillating the base element can include a motor 1762 (more specifically, a constant speed motor), and an eccentric shaft 1764 driven by the motor 1762, and coupled to the base element 1705. For example and as illustrated, the linkage for coupling to the base element 1705 may include a translatable rod 1766 and a mounting plate 1768 that detachably couples to the base element 1705. In some embodiments, the means for oscillating the base element 1705 may oscillate the base element 1705 and the flexible members 1725 at a rate of about 31 Hz (that is, 31 Hz±5 Hz)

The controlled stimulation device 1700 includes a fluid port 1770 for receiving one or more fluids from one or more fluid sources (not shown). The one or more fluids may be, for example, cooled air and a cryogenic liquid. The fluid port 1770 may be in fluid communication with one or more passageways. For example and as illustrated, the fluid port 1770 may be in fluid communication with a cooling passageway 1772, and flow of the fluid(s) in the cooling passageway 1772 may facilitate cooling components of the controlled stimulation device 1700. As another example and as illustrated, the fluid port 1770 may be in fluid communication with a delivery passageway 1774, and the delivery passageway 1774 may be in fluid communication with a nozzle (not shown) disposed at the treatment end of the device. As such, fluid may be dispensed via the delivery passageway 1774 and the nozzle prior to, during and/or after application of light energy to a patient.

Figure 21:
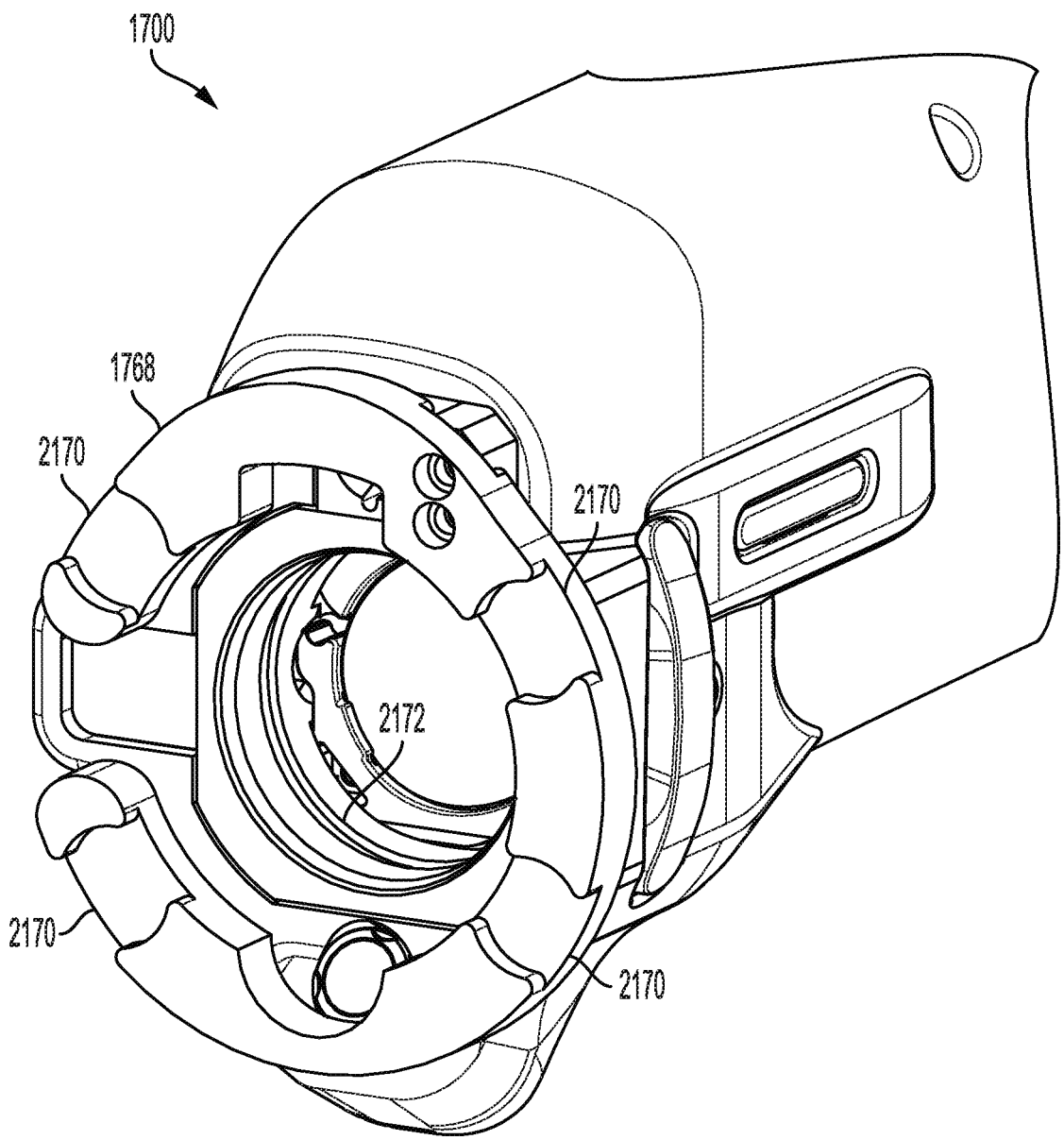
FIG. 21 is a perspective, cut-away view of the controlled stimulation device of FIG. 17 with a base element and a surface plate assembly being removed.

Referring to FIG. 21, there is shown a perspective, cut-away view of the treatment end of the controlled stimulation device 1700 with the base element 1705 and the skin surface reference element assembly 1738 being removed to illustrate the chassis features for detachably coupling to those components. That is, the treatment end of the controlled stimulation device 1700 includes a means for coupling to the base element 1705 and a means for coupling to the skin surface reference element assembly 1738. For example and as described above, the means for coupling to the base element 1705 may include the translatable rod 1766 (shown elsewhere) and the mounting plate 1768 that detachably couples to the base element 1705. More specifically, the mounting plate 1768 may magnetically couple to the base element 1705, and the mounting plate 1768 and the base element 1705 may include mating features that facilitate securing, properly positioning, and/or properly orienting the base element 1705 on the mounting plate 1768. For example and as illustrated, the mating features may include a plurality of recesses 2170 on the mounting plate 1768 that receive a plurality of protrusions on the base element 1705 (shown elsewhere). As illustrated, the recesses 2170 may be positioned and/or sized such that the base element 1705 may be coupled to the mounting plate 1768 in a single orientation. In other embodiments, the recesses 2170 may be positioned and/or sized such that the base element 1705 may be coupled to the mounting plate 1768 in various orientations. As another example, the mating features could be inverted relative to the above example. That is, the mating features could include a plurality of protrusions on the mounting plate 1768 that are received in a plurality of recesses on the base element 1705. The means for coupling to the skin surface reference element assembly 1738 may include, for example and as illustrated, a detent mechanism. More specifically, the controlled stimulation device 1700 may include a movable or deformable shoulder 2172 near the mounting plate 1768 and the skin surface reference element assembly 1738 may include a channel (shown elsewhere) for coupling to the shoulder 2172.

Figure 22:
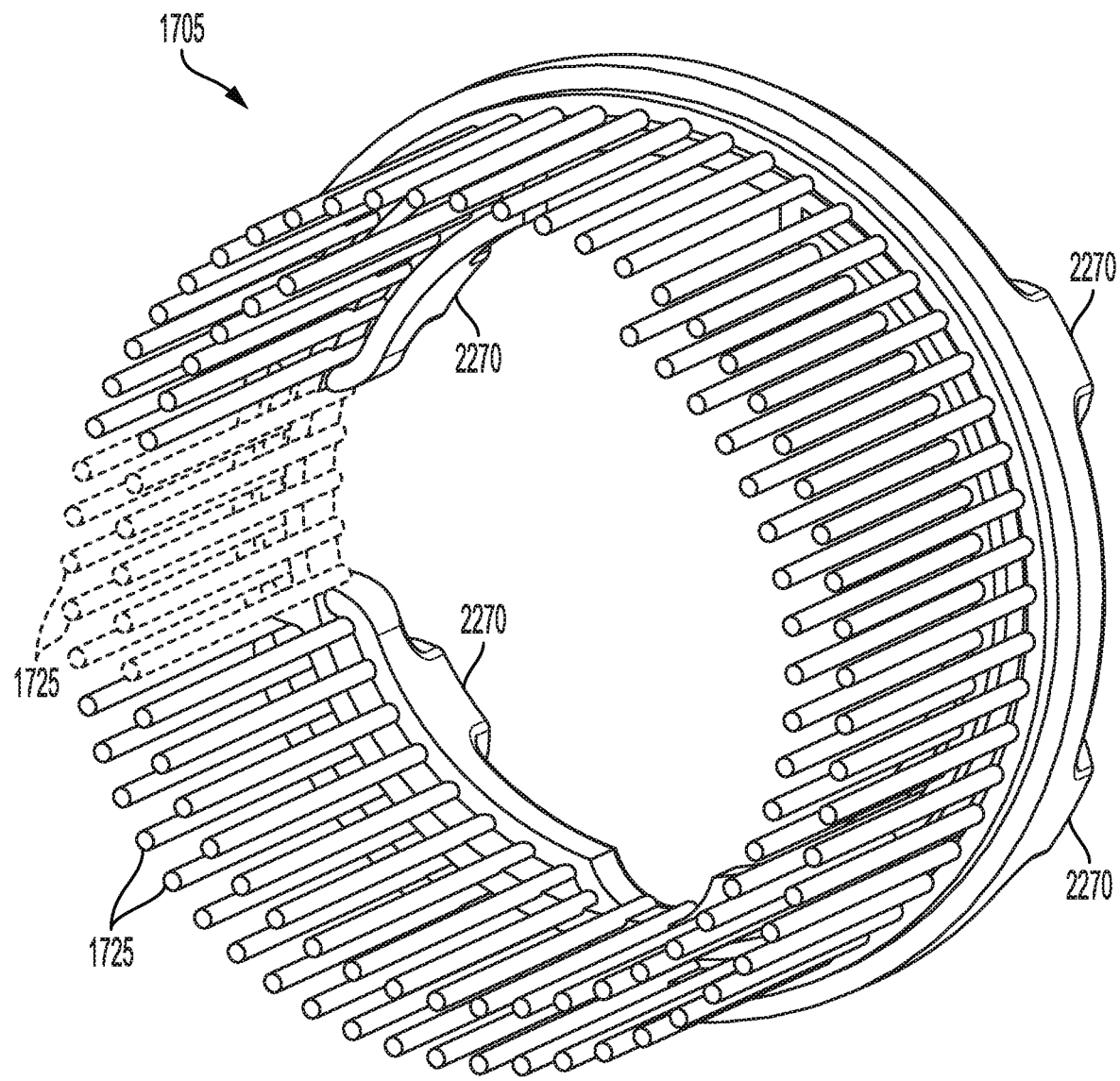
FIG. 22 is a perspective view of the base element of the controlled stimulation device of FIG. 17; the base element may have a closed ring-like shape (as illustrated, including the features shown in dashed lines) or an open ring-like shape (as illustrated, omitting the features shown in dashed lines)

Referring to FIG. 22, the base element 1705 and flexible elongated members 1725 are illustrated separately from the other components of the controlled stimulation device 1700. The base element 1705 with its elongated members 1725 can be provided as a single-use or disposable component (cartridge). As part of the mating features described above, the base element 1705 includes a plurality of protrusions 2270 that are received in the recesses 2170 of the mounting plate 1768. The base element 1705 may have a closed ring-like shape (as illustrated, including the features shown in dashed lines), such as a square, rectangular, circular, oval, ellipse, or orbital shape, or an open ring-like shape (as illustrated, omitting the features shown in dashed lines, to accommodate features of the skin surface reference element assembly 1738 as described in further detail below), such as an arch shape (e.g., a horseshoe shape) as viewed from one or both of the faces of the base element 1705. That is, the base element 1705 has an opening though which treatment energy, such as light, can be applied to the skin via the distal end 1735 of the device. The base element 1705, which is disposed radially outward from the emitted energy (e.g., light), therefore, partially or completely surrounds the applied energy. Because the flexible members 1725 are attached to base element 1705 and extend from the distal facing side of the base element 1705, the flexible members 1725 are disposed radially outward from the emitted energy (e.g., light) and partially or completely surrounds the applied energy. The flexible members 1725 may have any of the features, characteristics, dimensions and/or shapes described herein. Density can also be defined by the average bristle spacing, e.g., 2.5 mm or 0.1 inch (which can be referred to the norm or 100% density). The elongated members can also be packed more or less tightly, e.g., 200% density would be an average spacing of 1.25 mm or 0.05 inch or 50% density in which the elongate members would have an average spacing of 5 mm or 0.2". Thus, density by this measurement can vary from about 25% to about 300% of the normal distance between elongated members, as measured from center to center on the bristles. In certain embodiments, the flexible members 1725 may have a density of about 50% (that is, 50%±5%). In some embodiments, the base element carries about 35 flexible members 1725 (that is, 35 flexible members±5 flexible members).

Figure 23A:
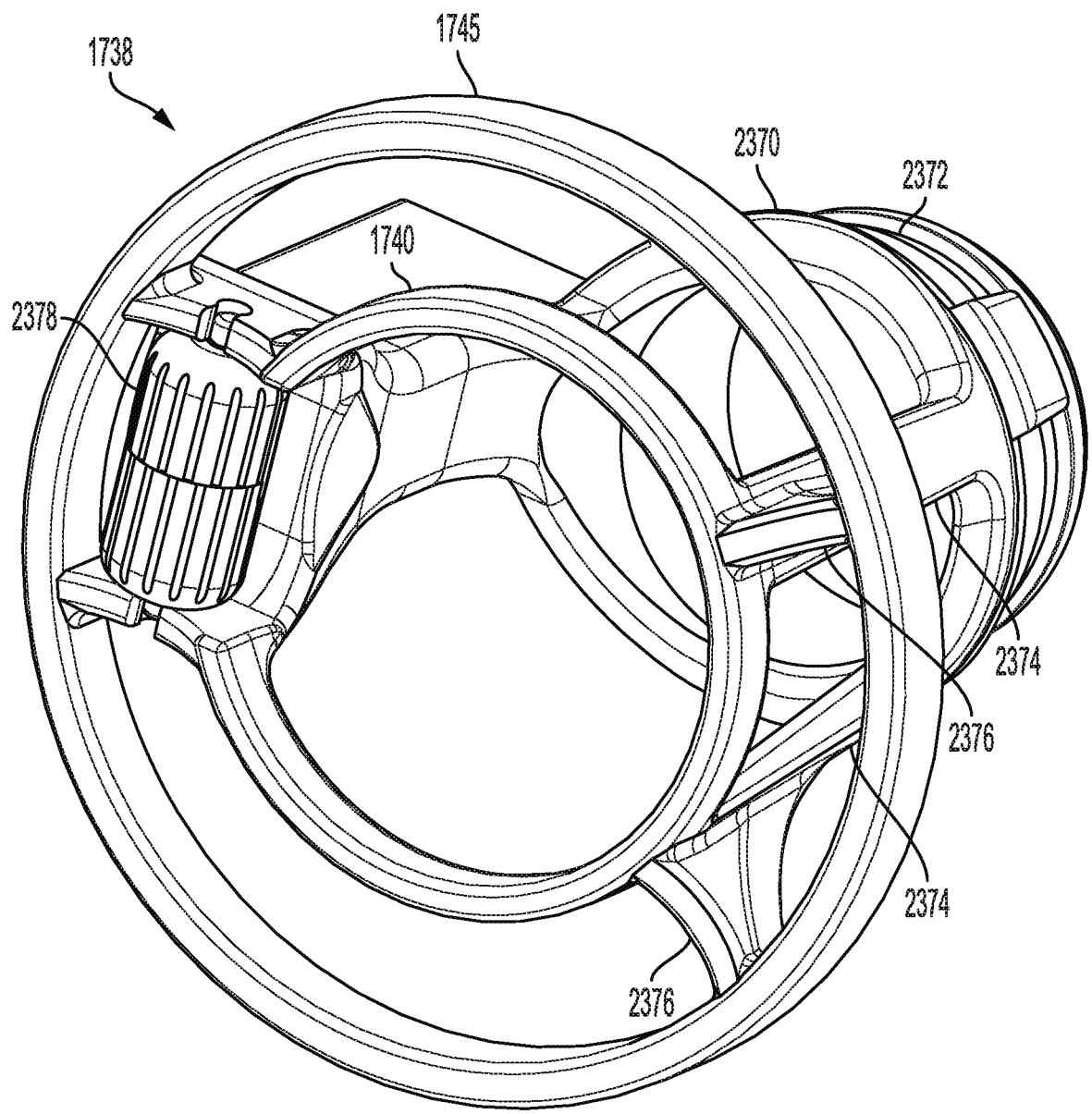
FIG. 23A is a perspective view of the surface plate assembly of the controlled stimulation device of FIG. 17.
Figure 23B:
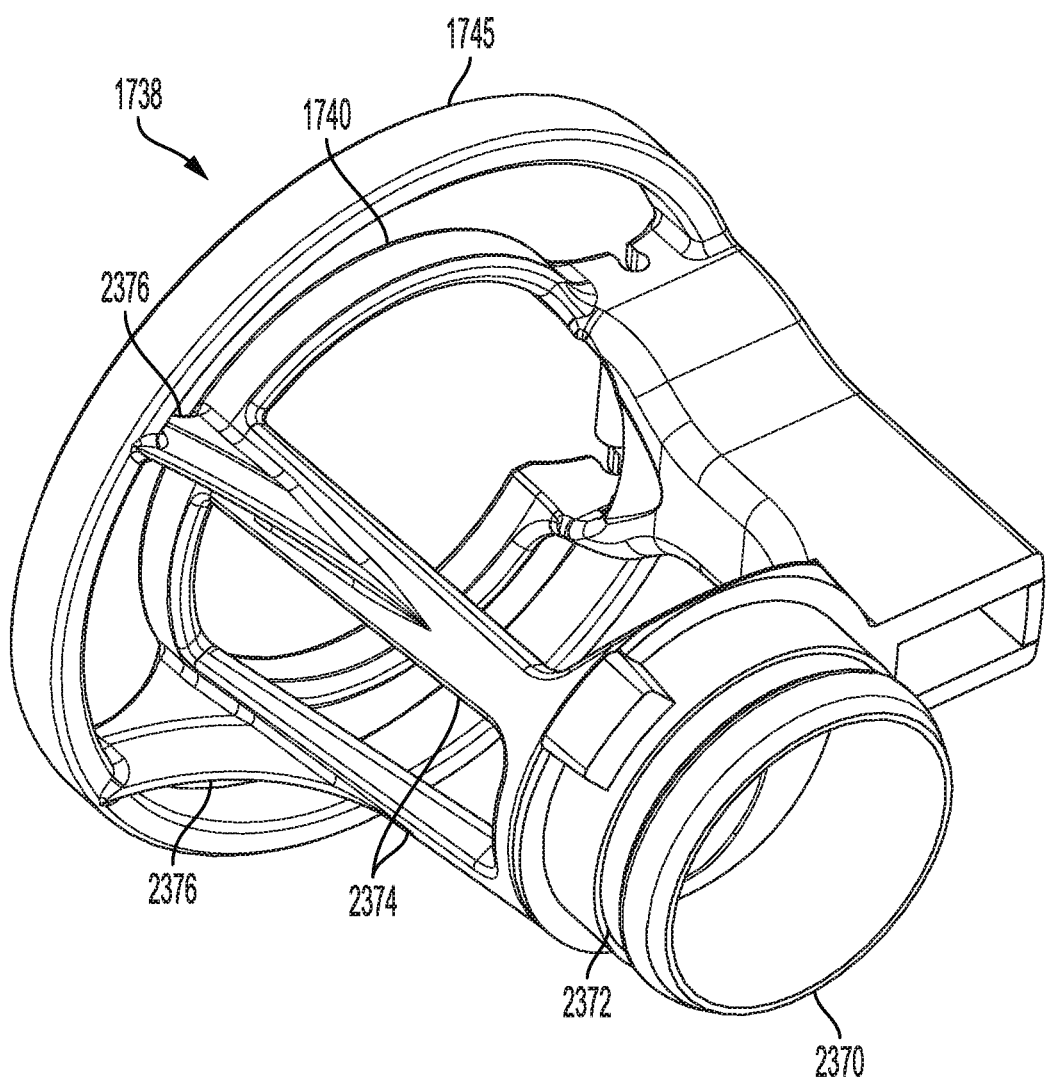
FIG. 23B is another perspective view of the surface plate assembly of the controlled stimulation device of FIG. 17.

Referring to FIGS. 23A and 23B, the skin surface reference element assembly 1738 is illustrated separately from the other components of the controlled stimulation device 1700. The skin surface reference element assembly 1738 may be provided as a multiple-use or reusable component. The skin surface reference element assembly 1738 includes a chassis hub 2370 that detachably couples to the controlled stimulation device 1700. The hub 2370 includes a portion of the detent mechanism described above. More specifically, the hub 2370 includes the channel 2372 for coupling to the shoulder 2172 of the controlled stimulation device 1700. The hub 2370 couples to the inner skin surface reference element 1740 via a plurality of legs 2374, and the inner skin surface reference element 1740 couples to the outer skin surface reference element 1745 via a plurality of arms 2376.

In some embodiments and as illustrated, the skin surface reference element assembly 1738 includes a distance determining device for determining a distance over which the surface reference assembly 1738 has moved over the skin of a patient. More specifically, the distance determining device may include a rotatable wheel 2378 and a rotational sensor (not shown—for example, an optical encoder or a hall effect sensor) for determining a distance over which the surface plate assembly 1738 has moved over the skin of a patient. In these embodiments, for example, the base element 1705 may have an open ring-like shape (for example, omitting the features shown in dashed lines in FIG. 22) to accommodate the distance determining device.

Figure 24:
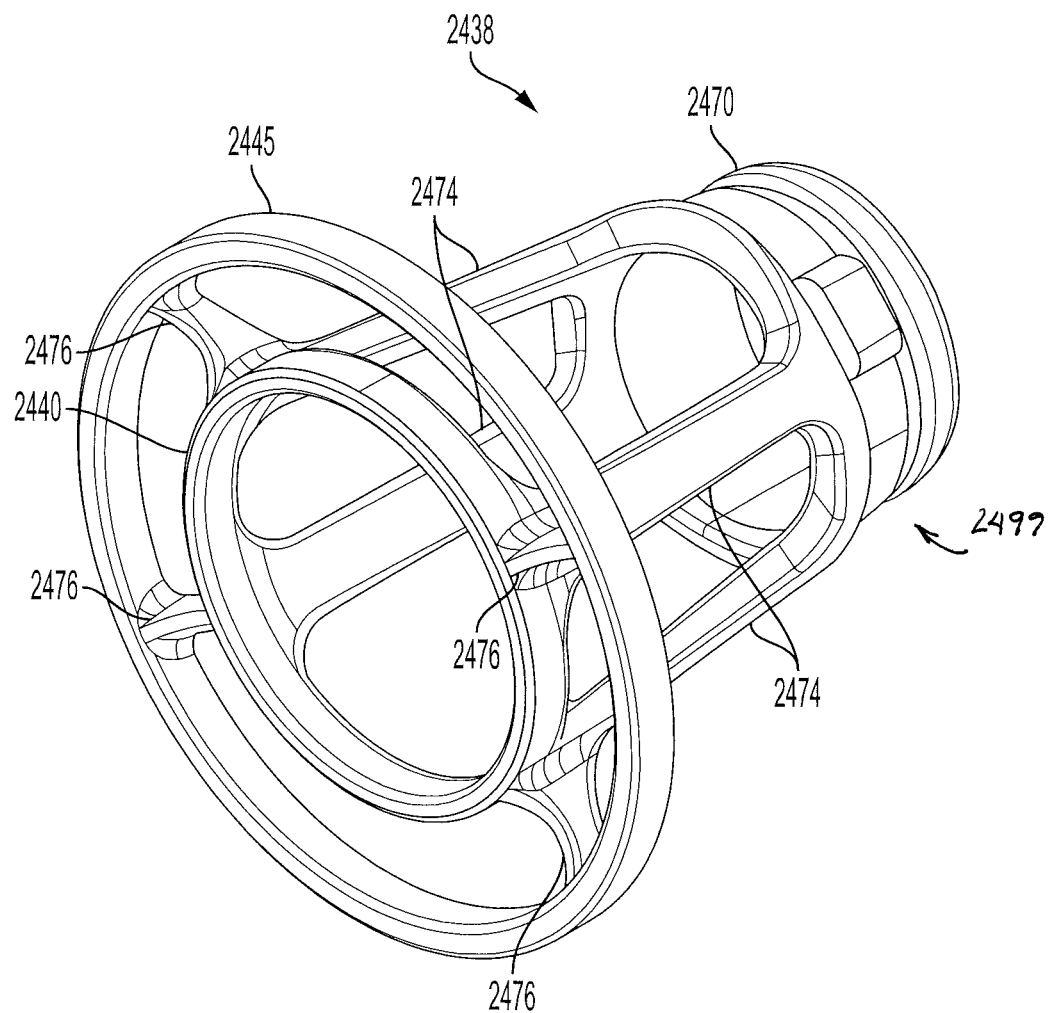
FIG. 24 is a perspective view of another example surface plate assembly for the controlled stimulation device of FIG. 17.

Referring to FIG. 24, another surface plate assembly 2438 is illustrated. The surface plate assembly 2438 may be used with the controlled stimulation device 1700 instead of the surface plate assembly 1738. The surface plate assembly 2438 lacks a distance determining device, but is otherwise generally similar to the surface plate assembly 1738. That is, the surface plate assembly 2438 includes a hub 2470, a plurality of chassis legs 2474 coupling the hub 2470 to an inner surface plate 2440, and a plurality of chassis arms 2476 coupling the inner surface plate 2440 to an outer surface plate 2445. In these embodiments, for example, the base element 1705 may have a closed ring-like shape (for example, including the features shown in dashed lines in FIG. 22).

Clinical Study

A clinical study was conducted to determine the relative efficacy of controlled stimulation devices having different characteristics and operating parameters. Specifically, nine patients were subjected to laser hair removal treatments using controlled stimulation devices. The patients were subjected to laser treatments according to two treatment types: (1) without activating the controlled stimulation features (that is, the elongated flexible members), and (2) while activating the controlled stimulation features. This permitted the patients to experience and characterize a difference in pain between the two situations. In the latter treatment type, the oscillation rate and density of the elongated flexible members were established as variables in order to determine the relative efficacy of controlled stimulation devices differing according to those variables.

Materials and Methods

The patients were subjected to laser hair removal treatments using the CLARITY™ dual wavelength alexandrite & Nd:YAG laser produced by Lutronic Corporation located in South Korea emitting laser pulses having a pulse duration of 3 ms and a wavelength 755 nm. The laser emitter was carried by a controlled stimulation device generally having the structure of the controlled stimulation device 1700 described above. The patients were subjected to such laser treatments according to two treatment types: (1) without oscillating the elongated flexible members and maintaining the flexible members in a fully-retracted position, and (2) while oscillating the elongated flexible members between the fully-retracted position and a fully-extended position, such that the distal ends of the flexible members contact the skin of the patients. In both of the first and second treatment types, about 18 laser pulses were delivered to the skin of the patients, and the controlled stimulation device delivered a cryogenic liquid to the skin of the patients immediately prior to each pulse. The bristles were 0.012 inch diameter Nylon 6/12. In the second treatment type, oscillation rate of the flexible members was varied between 23 Hz and 31 Hz, and the density of the elongated flexible members was varied between 50% (35 flexible members) and 100% (70 flexible members).

Each patient was subjected to the first and second treatment types in eight treatment areas on the leg below the knee, which were randomly selected from the twelve treatment areas. In each treatment area, the first treatment type was conducted in a randomly selected first zone (specifically, one of the medial half and the lateral half) and the second treatment type was conducted in a second zone (specifically, the other of the medial half and the lateral half). The order of conducting the first and second treatment types was also randomized. The first and second treatment types were conducted in two treatment areas for each patient while holding the above-identified variables constant.

In each treatment area, the patients indicated perceived differences in pain between the first and second treatment types using the ratings shown in Table 1.

TABLE 1

Ratings for perceived differences in pain between the first and second treatment types.

| Significantly Less Pain | Less Pain | No Difference in Pain | More Pain | Significantly More Pain |
|---|---|---|---|---|
| −2 | −1 | 0 | 1 | 2 |

Results

Results of the laser hair removal treatments are shown in Tables 2-5.

TABLE 2

Pain reduction proceeding from the first treatment type (elongated flexible members not activated) to the second treatment type (elongated flexible members) with an elongated flexible member density of 50% and an oscillation rate of 23 Hz. Specific locations of treatment areas I and II were randomized between patients.

| Patient No. | Treatment Area | Pain Reduction |
|---|---|---|
| 1 | I | −1 |
| 1 | II | −2 |
| 2 | I | −2 |
| 2 | II | −1 |
| 3 | I | −1 |
| 3 | II | −2 |
| 4 | I | 0 |
| 4 | II | −1 |

TABLE 2-continued

Pain reduction proceeding from the first treatment type (elongated flexible members not activated) to the second treatment type (elongated flexible members) with an elongated flexible member density of 50% and an oscillation rate of 23 Hz. Specific locations of treatment areas I and II were randomized between patients.

| Patient No. | Treatment Area | Pain Reduction |
|---|---|---|
| 5 | I | −2 |
| 5 | II | −2 |
| 6 | I | −1 |
| 6 | II | 0 |
| 7 | I | −1 |
| 7 | II | −1 |
| 8 | I | −1 |
| 8 | II | −1 |
| 9 | I | −2 |
| 9 | II | −1 |
| Total | | −22 |

TABLE 3

Pain reduction proceeding from the first treatment type (elongated flexible members not activated) to the second treatment type (elongated flexible members) with an elongated flexible member density of 50% and an oscillation rate of 31 Hz. Specific locations of treatment areas I and II were randomized between patients.

| Patient No. | Treatment Area | Pain Reduction |
|---|---|---|
| 1 | I | −2 |
| 1 | II | −2 |
| 2 | I | −2 |
| 2 | II | 0 |
| 3 | I | −1 |
| 3 | II | −2 |
| 4 | I | −1 |
| 4 | II | −1 |
| 5 | I | −2 |
| 5 | II | −2 |
| 6 | I | −2 |
| 6 | II | −1 |
| 7 | I | −2 |
| 7 | II | 0 |
| 8 | I | −2 |
| 8 | II | 0 |
| 9 | I | −1 |
| 9 | II | −1 |
| Total | | −24 |

TABLE 4

Pain reduction proceeding from the first treatment type (elongated flexible members not activated) to the second treatment type (elongated flexible members) with an elongated flexible member density of 100% and an oscillation rate of 23 Hz. Specific locations of treatment areas I and II were randomized between patients.

| Patient No. | Treatment Area | Pain Reduction |
|---|---|---|
| 1 | I | 0 |
| 1 | II | −1 |
| 2 | I | −2 |
| 2 | II | −1 |
| 3 | I | −1 |
| 3 | II | −2 |
| 4 | I | −1 |
| 4 | II | −1 |
| 5 | I | −1 |
| 5 | II | −2 |

TABLE 4-continued

Pain reduction proceeding from the first treatment type (elongated flexible members not activated) to the second treatment type (elongated flexible members) with an elongated flexible member density of 100% and an oscillation rate of 23 Hz. Specific locations of treatment areas I and II were randomized between patients.

| Patient No. | Treatment Area | Pain Reduction |
|---|---|---|
| 6 | I | −1 |
| 6 | II | −1 |
| 7 | I | −1 |
| 7 | II | −1 |
| 8 | I | −1 |
| 8 | II | −1 |
| 9 | I | −1 |
| 9 | II | −2 |
| Total | | −21 |

TABLE 5

Pain reduction proceeding from the first treatment type (elongated flexible members not activated) to the second treatment type (elongated flexible members) with an elongated flexible member density of 100% and an oscillation rate of 31 Hz. Specific locations of treatment areas I and II were randomized between patients.

| Patient No. | Treatment Area | Pain Reduction |
|---|---|---|
| 1 | I | −2 |
| 1 | II | −2 |
| 2 | I | −2 |
| 2 | II | −1 |
| 3 | I | 0 |
| 3 | II | −2 |
| 4 | I | −1 |
| 4 | II | −1 |
| 5 | I | −2 |
| 5 | II | −2 |
| 6 | I | 0 |
| 6 | II | −1 |
| 7 | I | −1 |
| 7 | II | 0 |
| 8 | I | −1 |
| 8 | II | −1 |
| 9 | I | −2 |
| 9 | II | −1 |
| Total | | −22 |

The results suggest that controlled stimulation devices including oscillating elongated flexible members arranged in various densities and operated at various oscillation rates provide a perceived reduction in pain during dermal laser treatments. Further, the results suggest that controlled stimulation devices including oscillating elongated flexible members arranged in a density of 50% and operated at an oscillation rate of 31 Hz provide a relatively high perceived reduction in pain during laser hair removal treatments. It is believed that otherdensities or oscillation rates, including similar densities and oscillation rates (for example, about 50% (that is, 50%±5%) or about 31 Hz (that is, 31 Hz±5 Hz, respectively) would also provide similar perceived reductions in pain.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. For example, the devices and methods provided in this disclosure may be used in combination with other devices, such as Lutronic's Action II Petit Lady™ device used for treating vaginal relaxation syndrome (VRS) and stress urinary incontinence (SUI). The elongated flexible members could be oriented around the central probe of the Petit Lady™ device and move away and towards the tissue surrounding the outer guide portions, for use to reduce pain and treat such tissue. This example illustrates how the devices and methods of the present disclosure could also be adapted and repurposed for insertion into any natural human orifice or passageway, or any surgical opening in an open or closed surgical procedure, for use in applying energy, and/or treats a condition or otherwise described herein.

Penetration of the elongated flexible members into tissue may also be useful in stimulating the body's natural healing response to rejuvenate skin or other tissue. Moreover, different features of the present disclosure can be used to achieve a broad set of goals, including any combination of the following: mitigating pain created by or a partial result of a treatment device; imparting a therapeutic effect on skin and/or other tissue on or in the body; temporarily or for an extended period, assisting in the management, mitigation or otherwise reducing or relieving pain caused by an injury or condition (e.g., other than by a treatment device).

This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A controlled stimulation device for use during a treatment procedure, comprising:
   at least one skin reference element having a distal end that defines a skin surface plane when placed in contact with a region of skin to be treated,
   a base element movable relative to the skin reference element and
   a plurality of elongated flexible members coupled to the base element, such that distal ends of the elongated flexible members can move between at least two positions, one position being a stowed position behind or proximal to the distal end of the skin reference element and the other position being a deployed position in which the distal ends of the elongated flexible members protrude to contact or penetrate the skin region.

2. The device of claim 1 wherein the distal ends of the elongate members protrude beyond the distal end of the skin reference element in their deployed position.

3. The device of claim 1 further comprising a chassis to which the at least one skin reference element can be coupled, said chassis having a mount that couples to the base element such that the distal ends of elongated elements can move between said stowed position and said deployed position.

4. The device of claim 3, wherein the chassis further comprises a mounting plate that magnetically couples to the base element.

5. The device of claim 1, wherein the skin surface element is disposed distally relative to said base element.

6. The device of claim 1, wherein the device is further adapted to couple with a skin treatment device.

7. The device of claim 6, wherein the skin treatment device comprises a light energy source.

8. The device of claim 6, wherein the skin treatment device comprises radio frequency electrical energy source.

9. The device of claim 6, wherein the skin treatment device comprises a mechanical stimulatory device.

10. The device of claim 1, wherein the base element further comprises an aperture through which energy can be applied to the skin and the elongated members are arranged to at least partially surround the aperture.

11. The device of claim 1, wherein the device further comprises a motor coupled to the base element via a linkage for inducing movement of the base element.

12. The device of claim 10, wherein the linkage imparts axial motion to the base element.

13. The device of claim 10, wherein the linkage further comprises a reciprocating drive shaft.

14. The device of claim 10, wherein the linkage comprises a cylindrical or tangent cam coupled to a drive shaft, said drive shaft being coupled to the base element.

15. The device of claim 1, wherein the distal ends of the elongated flexible members have a round point, a star point, a cross point, a tapered face, a beveled face, a multi-facet face, a conical, a spherical, an elliptical, or a hyper-elliptical shape.

16. The device of claim 1, wherein said plurality of elongated flexible members have a length in a range of 0.05 millimeters (mm) to 150 mm.

17. The device of claim 1, wherein said plurality of elongated flexible members have a cross-sectional area in a range of 0.02 members per millimeters$^2$ to 20 members per millimeters$^2$.

18. The device of claim 1, wherein one or more of said plurality of elongated flexible members has an end face that is beveled at an angle between 30 degrees and 60 degrees.

19. The device of claim 1, wherein said elongated flexible members have a diameter in a range of 25 microns to 200 microns.

20. The device of claim 1, wherein said elongated flexible members comprise at least one of a metal and a polymer.

21. The device of claim 20, wherein said metal comprises stainless steel.

22. The device of claim 20, wherein said polymer comprises at least one of nylon, polyester, polybutylene terephthalate (PBT), polyphenylene sulfide (PPS), and fluorinated polymers.

23. The device of claim 1, wherein at least one of said elongated flexible members bends upon application of a force in a range of 0.05 milliNewtons (mN) to 3000 mN thereto, wherein the force is applied normal to at least one of a proximal end and a distal end of said member.

24. The device of claim 1, wherein at least one of said elongated flexible members bends upon application of a pressure in a range of $4.1 \times 10^{-8}$ newtons/millimeters$^2$ to $6.1 \times 10^3$ newtons/millimeters$^2$ thereto, wherein said pressure is applied normal to at least one of a proximal end or a distal end of said member.

25. The device of claim 1, wherein the elongated flexible members are configured such that upon bending, a linear distance between a proximal end and a distal end of flexible member is reduced between 0.1 millimeters (mm) and 10 mm.

26. The device of claim 1, wherein a surface density of said elongated flexible members is in a range of 0.2 filaments per millimeters$^2$ to 4 filaments per millimeters$^2$.

27. The device of claim 11, wherein said motor is configured to cause periodic movement of said base element at a rate in a range of 1 hertz (Hz) to 1000 Hz.

28. The device of claim 1, wherein a number of said elongated flexible members is in a range of 1 to 10,000.

29. The device of claim 1, wherein said at least two positions are separated by a distance in a range of 0.1 millimeters (mm) to 30 mm.

30. The device of claim 28, wherein said at least two positions are separated by a distance in a range of 0.25 millimeters (mm) to 7.5 mm.

31. The device of claim 1, wherein said elongated flexible members at least partially surround said skin reference element.

32. The device of claim 1, wherein said skin reference element at least partially surrounds said elongated flexible members.

33. The device of claim 1, wherein said plurality of elongated flexible members comprise at least two subsets, wherein the flexible members in one subset differ in at least one property relative to the flexible members in the other subset.

34. The device of claim 33, wherein the elongated flexible members in one subset have a different length relative to the elongated flexible members in the other subset.

35. The device of claim 33, wherein distal ends of the elongated flexible members in one subset have a different shape relative to distal ends of the elongated flexible members in the other subset.

36. The device of claim 1, wherein said base element comprises a plurality of elements configured for independent movement so that different subsets of said elongated flexible members coupled to said plurality of elements can be moved independently.

37. The device of claim 1, wherein said base is rotatable about a longitudinal axis thereof so as to provide radial movement of said elongated flexible members.

38. A cartridge for a controlled stimulation device including a skin treatment device having at least one skin reference element with a distal end that defines a skin surface plane when placed in contact with a region of skin to be treated, the cartridge comprising a base element having a plurality of elongated flexible members, said base element being configured to removably engage with the skin treatment device, the base element being movable when mounted in the skin treatment device such that distal ends of the elongated flexible members can move between at least two positions, one position being a stowed position behind or proximal to the distal end of the skin reference element and the other position being a deployed position in which the distal ends of the elongated flexible members protrude distally to contact or penetrate the skin region.

39. The cartridge of claim 38 wherein the distal ends of the elongate members protrude beyond the distal end of the skin reference element in their deployed position.

40. The cartridge of claim 38, wherein the cartridge further comprises a mount that couples to the base element such that the distal ends of elongated elements can move between said stowed position and said deployed position.

41. The cartridge of claim 38, wherein the treatment device comprises an energy source for generating treatment energy and each of the base element and the skin reference element comprises an aperture to allow passage of said treatment energy to the skin.

42. The cartridge of claim 40, wherein said energy source comprises a light source or a radio frequency energy source.

43. The cartridge of claim 38, wherein the treatment device comprises a mechanical stimulatory device.

44. The cartridge of claim 38, wherein said skin surface element is disposed distally relative to said base element.

45. The cartridge of claim 38, wherein said cartridge is configured to couple to a chassis of said skin treatment device.

46. The cartridge of claim 38, wherein said cartridge further comprises a motor coupled to the base element via a linkage for inducing movement of the base element.

47. The cartridge of claim 46, wherein said motor and the linkage are removably and replaceably coupled to an outer surface of said chassis of the treatment device.

48. The cartridge of claim 46, wherein said linkage imparts axial motion to the base element.

49. The cartridge of claim 46, wherein said linkage comprises a cylindrical or tangent cam coupled to a drive shaft, said drive shaft being coupled to the base element.

50. The cartridge of claim 38, wherein the distal ends of the elongated flexible members comprise at least one of a round point, a star point, a cross point, a tapered face, a beveled face, a multi-facet face, a conical shape, a spherical shape, an elliptical shape, and a hyper-elliptical shape.

51. The cartridge of claim 38, wherein said plurality of elongated flexible members have a length in a range of 0.05 millimeters (mm) to 150 mm.

52. The cartridge of claim 38, wherein said plurality of elongated flexible members have a cross-sectional area in a range of 0.02 millimeters$^2$ to 20 millimeters$^2$.

53. The cartridge of claim 38, wherein one or more of said plurality of elongated flexible members has an end face that is beveled at an angle between 30 degrees and 60 degrees.

54. The cartridge of claim 38, wherein said elongated flexible members have a diameter in a range of 25 microns to 200 microns.

55. The cartridge of claim 38, wherein said elongated flexible members comprise at least one of a metal and a polymer.

56. The cartridge of claim 55, wherein said metal comprises stainless steel.

57. The cartridge of claim 56, wherein said polymer comprises at least one of nylon, polyester, polybutylene terephthalate (PBT), polyphenylene sulfide (PPS), and fluorinated polymers.

58. The cartridge of claim 38, wherein at least one of said elongated flexible members bends upon application of a force in a range of 0.05 milliNewtons (mN) to 300 mN thereto, wherein the force is applied normal to at least one of a proximal end and a distal end of said member.

59. The cartridge of claim 38, wherein at least one of said elongated flexible members bends upon application of a pressure in a range of $4.1 \times 10^{-8}$ newtons/millimeters$^2$ to $6.1 \times 10^3$ newtons/millimeters$^2$ thereto, wherein said pressure is applied normal to at least one of a proximal end or a distal end of said member.

60. The cartridge of claim 59, wherein the elongated flexible members are configured such that upon bending a linear distance between a proximal end and a distal end of the flexible member is reduced between 0.1 millimeters (mm) to 10 mm.

61. The cartridge of claim 38, wherein a surface density of said elongated flexible members is in a range of 0.2 filaments per millimeters$^2$ to 4 filaments per millimeters$^2$.

62. The cartridge of claim 46, wherein said motor is configured to cause periodic movement of said base element at a rate in a range of 1 hertz (Hz) to 1000 Hz.

63. The cartridge of claim 38, wherein a number of said elongated flexible members is in a range of 1 to 10,000.

64. The cartridge of claim 38, wherein said at least two positions are separated by a distance in a range of 0.1 millimeters (mm) to 15 mm.

65. The cartridge of claim 38, wherein said at least two positions are separated by a distance in a range of 0.25 millimeters (mm) to 7.5 mm.

66. The cartridge of claim 38, wherein said elongated flexible members at least partially surround said skin reference element.

67. The cartridge of claim 38, wherein said skin reference element at least partially surrounds said elongated flexible members.

68. The cartridge of claim 38, wherein said plurality of elongated flexible members comprise at least two subsets, wherein the flexible members in one subset differ in at least one property relative to the flexible members in the other subset.

69. The cartridge of claim 38, wherein the elongated flexible members in one subset have a different length relative to the elongated flexible members in the other subset.

70. The cartridge of claim 38, wherein distal ends of the elongated flexible members in one subset have a different shape relative to distal ends of the elongated flexible members in the other subset.

71. The cartridge of claim 38, wherein said base element comprises a plurality of elements configured for independent movement so that different subsets of said elongated flexible members coupled to said plurality of elements can be moved independently.

72. The cartridge of claim 38, wherein said base element is rotatable about a longitudinal axis thereof so as to provide radial movement of said elongated flexible members.

73. The cartridge of claim 38 wherein the cartridge is disposable.

74. The cartridge of claim 38 wherein the cartridge is reusable.

75. A method of controlled stimulation during skin treatment, comprising:
contacting a region of skin with at least one skin reference element having a distal end that defines a skin surface plane, and
deploying a plurality of elongated flexible members to repeatedly contact or penetrate the skin, the plurality of elongated flexible members being attached to a base element that is movable such that distal ends of the elongated flexible members can move between at least two positions, one position being a stowed position behind or proximal to the distal end of the skin reference element and the other position being a deployed position in which the distal ends of the elongated flexible members protrude to contact or penetrate the skin region.

76. The method of claim 75, wherein the movement of the distal ends of the elongated flexible members is a repetitive motion at a frequency in the range of 1 hertz (Hz) to 1000 Hz.

77. The method of claim 75, wherein the movement of the distal end of the elongated flexible members comprises an axial oscillatory motion.

78. The method of claim 75, wherein the movement of the distal end of the elongated flexible members comprises a rotary motion.

79. The method of claim 75, wherein a portion of the elongated members are designed to have limited penetration into the skin to effect controlled stimulation, whereas another portion of elongate members are designed to have a deeper penetration into the skin to effect skin treatment.

80. The method of claim 79, wherein the elongate members that provide the controlled stimulation effect are configured to have a penetration of less than 50 microns (µm) into the skin.

81. The method of claim 79, wherein the elongate members that provide the skin treatment effect are configured to have a penetration of 100 microns to 500 microns into the skin.

82. A dermatological treatment system, comprising:
a handpiece for delivering energy from an energy source for skin treatment, and
a controlled stimulation device for reducing pain perception during the treatment, said controlled stimulation device being configured for removable and replaceable coupling to said handpiece,
wherein said controlled stimulation device comprises:
at least one skin reference element having a distal end that defines a skin surface plane when placed in contact with a region of skin to be treated,
a base element movable relative to the skin reference element, and
a plurality of elongated flexible members coupled to the base element, such that distal ends of the elongated flexible members can move between at least two positions, one position being a stowed position at or behind the distal end of the skin reference element and the other position being a deployed position in which the distal ends of the elongated flexible members protrude distally to contact or penetrate the skin region.

83. The treatment system of claim 82, further comprising a controller for controlling and coordinating activation of said energy source and said controlled stimulation device.

84. The treatment system of claim 82, wherein said energy source is a light energy source.

85. The treatment system of claim 82, wherein said energy source is a radio frequency energy source.

86. The treatment system of claim 82, further comprising a motor disposed in any of said handpiece and said controlled stimulation device, said motor being coupled via a linkage to said base element to induce movement thereof.

87. The treatment system of claim 86, wherein said motor is disposed in a sleeve configured for removable and replaceable coupling to said handpiece.

* * * * *